United States Patent [19]
Holmes

[11] Patent Number: 5,917,016
[45] Date of Patent: *Jun. 29, 1999

[54] PHOTOLABILE COMPOUNDS AND METHODS FOR THEIR USE

[75] Inventor: Christopher P. Holmes, Sunnyvale, Calif.

[73] Assignee: Affymax Technologies N.V., Greenford, United Kingdom

[ * ] Notice: This patent is subject to a terminal disclaimer.

[21] Appl. No.: 09/006,547

[22] Filed: Jan. 13, 1998

Related U.S. Application Data

[63] Continuation-in-part of application No. 08/265,090, Jun. 23, 1994, Pat. No. 5,549,974, and application No. 08/374,492, Jan. 17, 1995, Pat. No. 5,679,773.

[51] Int. Cl.$^6$ .................................................. C07K 1/04
[52] U.S. Cl. .................... 530/334; 530/333; 530/345; 430/56; 430/270
[58] Field of Search .................... 530/334, 333, 530/345; 430/56, 270

[56] References Cited

U.S. PATENT DOCUMENTS

| | | | |
|---|---|---|---|
| 4,593,029 | 6/1986 | Venuti et al. | 514/267 |
| 4,728,502 | 3/1988 | Hamill | 422/116 |
| 5,143,854 | 9/1992 | Pirrung et al. | 436/518 |
| 5,288,514 | 2/1994 | Ellman | 427/2 |
| 5,424,186 | 6/1995 | Fodor | 435/6 |
| 5,482,719 | 1/1996 | Guillet | 424/486 |
| 5,549,974 | 8/1996 | Holmes | 428/403 |
| 5,679,773 | 10/1997 | Holmes | 530/334 |

FOREIGN PATENT DOCUMENTS

| | | |
|---|---|---|
| 1 472 937 | 5/1977 | United Kingdom . |
| 90/00626 | 1/1990 | WIPO . |
| 90/15070 | 12/1990 | WIPO . |
| 92/10092 | 6/1992 | WIPO . |
| 93/10162 | 5/1993 | WIPO . |
| 93/10183 | 5/1993 | WIPO . |
| 95/04160 | 2/1995 | WIPO . |

OTHER PUBLICATIONS

Abraham et al., 1991, Tetrahedron Letters, 32(5):577–580.
Barany et al., 1985, J. Am. Chem. Soc., 107:4936–4942.
Bellof et al., 1985, Chimia, 39(10):317–320.
Bush et al., 1988, Amer. J. Optometry Physiol. Optics, 65(9):722–728.
Cook et al., 1994, Tetrahedron Letters, 35(37):6777–6780.
Dugave et al., 1994, Tetrahedron Letters, 35(51): 9557–9560 Synthesis of activated disulfide adducts containing a 4–diazocyclohexa–2,5–dienone precursor for photoaffinity labelling.
Fodor et al., 1991, Science, 251:767–777 Light–directed, spatially adressable parallel chemical synthesis.
Frank et al., 1988, Tetrahedron, 44:6031–6040 Simultaneous multiple peptide synthesis under continuous flow conditions on cellulose paper discs as segmental solid supports.
Geysen et al., 1987, J. Immun. Meth., 102:259–274 Strategies for epitome analysis using peptide synthesis.
Green et al., 1975, Adv. Protein Chem., 29:85–133.
Green et al., 1991, *Protective Groups in Organic Synthesis*, John Wiley: New York, pp. 1–362, see pp. 27, 62, 88, 89, 315, 349 and 362.
Jones et al., 1987, Chemical Abstracts, 106(13):102224 Inhibitors of cyclic AMP phosphodiesterase: 1. Analogs of cilostamide and anagrelide.
Jones et al., 1987, J. Medicinal Chemistry, 30(2):295–303.
Merrifield, 1963, J. Am. Chem. Soc., 85:2149–2154 Solid phase peptide synthesis. I . The synthesis of a peptide.
Nagakura et al., 1975, Heterocycles, 3(6):453–457.
Rajasekharan Pillai et al., 1980, J. Org. Chem., 45(26):5364–5370 New, easily removable poly(ethylene glycol) supports for liquid–phase method of peptide synthesis.
Rich et al., 1975, J. Am. Chem. Soc., 97:1575–1579 Preparation of a new o–nitrobenzyl resin for solid–phase synthesis of tert–butyloxycarbonyl–protected peptide acids.
Safar et al., Jun. 1994, 24th National Medicinal Chemistry Symposium, P206 Generation of Peptide–like libraries using amino acid–like subunits.
Surrey et al., 1958, J. Am. Chem Soc., 80:3469–3471.
Teague, 1996, Tetrahedron Letters, 37(32):5751–5754 Facile synthesis of a o–nitrobenzyl photolabile linker for combinatorial chemistry.
Wang, 1976, J. Org. Chem., 41(20):3258–3261.
Yoo and Greenberg, 1995, *J. Org. Chem.*, 60:3358–3364 Synthesis of oligonucleotides containing 3–alkyl carboxylic acids using universal, photolabile solid phase synthesis supports.

*Primary Examiner*—Cecilia J. Tsang
*Assistant Examiner*—David Lukton
*Attorney, Agent, or Firm*—Lauren L. Stevens

[57] ABSTRACT

Novel compounds are provided which are useful as photocleavable linking groups in solid phase synthesis. Compositions incorporating these linking groups and methods for their use are also described.

12 Claims, 6 Drawing Sheets

PHOTOLABILE COMPOUNDS AND METHODS FOR THEIR USE

CROSS-REFERENCE

This application is a continuation-in-part of copending U.S. patent application Ser. No. 08/265,090, filed Jun. 23, 1994, now U.S. Pat. No. 5,549,974, and a continuation-in-part of copending U.S. patent application Ser. No. 08/374,492, filed Jan. 17, 1995, now U.S. Pat. No. 5,679,773, each of which is expressly incorporated herein by reference for all purposes.

BACKGROUND OF THE INVENTION

The present invention is related to the area of chemical synthesis. More specifically, one embodiment of the present invention provides certain photolabile compounds and methods for their use as photocleavable linkers.

The use of a photolabile molecule as a linker to couple peptides to solid supports and to facilitate the subsequent cleavage reaction has received considerable attention during the last two decades. Photolysis offers a mild method of cleavage which complements traditional acidic or basic cleavage techniques. See, e.g., Lloyd-Williams et al. (1993) *Tetrahedron* 49: 11065–11133. The rapidly growing field of combinatorial organic synthesis (see, e.g., Gallop et al. (1994) *J. Med. Chem.* 37: 1233–1251; and Gordon et al. (1994) *J. Med. Chem.* 37: 1385–1401) involving libraries of peptides and small molecules has markedly renewed interest in the use of photolabile linkers for the release of both ligands and tagging molecules.

A phenacyl based linking group (see 1 below) has been described. See Wang, (1976) *J. Org. Chem.* 41: 3258.

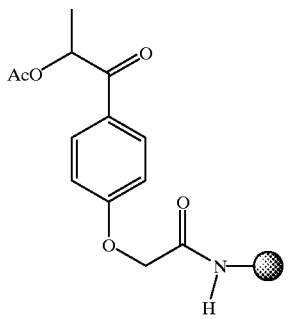

1

An ortho-nitrobenzyl support (see 2 below) derived from 4-bromomethyl-3-nitrobenzoic acid has been widely employed as a photolabile support for the generation of both peptide acids and amides. See Rich et al. (1975) *J. Am. Chem. Soc.* 97: 1575–1579 and Hammer et al. (1990) *Int. J. Peptide Protein Res.* 36: 31–45.

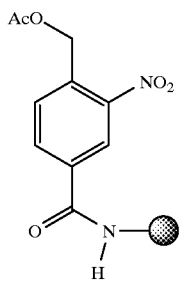

2

Photolabile support 2, though useful, does suffer from several limitations. For example, workers have been unable to obtain high yields of methionine-containing peptides from the support without substantial contamination with methionine sulfoxide. See Rich supra and Hammer supra. One solution has been to employ methionine sulfoxide throughout the peptide assembly and to subsequently reduce back to methionine to avoid any ambiguities associated with partial oxidation (see, Lloyd-Williams et al. (1991) *J. Peptide Protein Res.* 37: 58–60 and Lloyd-Williams et al. (1993) *Tetrahedron* 49: 10069–10078), but this clearly detracts from the usefulness of the technique. This support also suffers from unduly slow cleavage kinetics, with typical photolysis times in organic solvents ranging from 12 to 24 hours. Moreover, photolysis of the support generates a reactive and chromogenic nitroso-aldehyde on the support which can trap liberated compounds and may act as an internal light filter to slow the rate of cleavage. See Patchnornik et al. (1970) *J. Am. Chem. Soc.* 92: 6333–6335.

Pillai and co-workers have described an α-methyl-ortho-nitrobenzyl support designed to eliminate formation of the nitroso-aldehyde, but they observed inefficient release of peptides longer than five residues due to poor swelling of the resin. See Ajayaghosh et al. (1988) *Tetrahedron* 44: 6661–6666.

In the course of optimizing the photolithographic synthesis of both peptides (see Fodor et al. (1991) *Science* 251: 767–773) and oligonucleotides (see Pease et al. (1994) *Proc. Natl. Acad. Sci. USA* 91: 5022–5026, we had occasion to explore the use of a variety of ortho-benzyl compounds as photolabile protecting groups. See PCT patent publication Nos. WO 90/15070, WO 92/10092, and WO 94/10128; see also U.S. patent application Ser. No. 07/971,181, filed Nov. 2, 1992, and Ser. No. 08/310,510, filed Sep. 22, 1994; Holmes et al. (1994) in *Peptides: Chemistry, Structure and Biology* (*Proceedings of the* 13th *American Peptide Symposium*): Hodges et al. Eds.; ESCOM: Leiden; pp. 110–12, each of these references is incorporated herein by reference for all purposes. Examples of these compounds included the 6-nitroveratryl derived protecting groups, which incorporate two additional alkoxy groups onto the benzene ring. Introduction of an α-methyl onto the benzylic carbon facilitated the photolytic cleavage with >350 nm UV light and resulted in the formation of a nitroso-ketone.

Photolabile amide protecting groups for C-termini of peptides which rely on the same basic ortho-nitro benzyl chemistry have also been reported. See Henricksen et al. (1993) *Int. J. Peptide Protein Res.* 41: 169–180; Ramesh et al. (1993) *J. Org. Chem.* 58: 4599–5605; Pillai (1980) *Synthesis* 1–26; and Pillai et al. (1979) *Tetrahedron Lett.* 3409–3412. See also Bellof and Mutter (1985) *Chimia* 39: 10.

A photocleavable linker should be stable to variety of reagents (e.g., piperidine, TFA, and the like); be rapidly cleaved under mild conditions; and not generate highly reactive byproducts. The present invention provides such linkers.

SUMMARY OF THE INVENTION

The present invention provides new compounds and methods which find application in solid phase synthesis including the preparation of peptides or small ligand molecules, and libraries thereof, as well as in the preparation of high-density arrays of diverse polymer sequences such as diverse peptides and oligonucleotides. The compounds of the present invention are those which are typically referred to as linking groups, linkers or spacers.

According to a first aspect of the invention, novel compounds are provided which are useful as linking groups in solid phase synthesis. These compounds are useful as linking groups which are photochemically cleavable. Preferred linking groups have the formula:

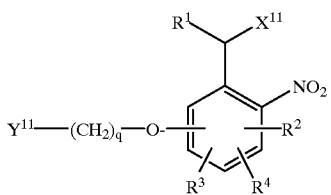

wherein, $R^1$ is hydrogen, $C_1$–$C_8$ alkyl, aryl or arylalkyl; $R^2$, $R^3$ and $R^4$ are each independently hydrogen, $C_1$–$C_8$ alkyl, or $C_1$–$C_8$ alkoxy; $X^{11}$ and $Y^{11}$ are each independently selected from the group consisting of halogen, —SH, —SP, —OH, —OP, —NH$_2$, —NHP, in which P is a suitable protecting or activating group, and —NR$^5$R$^6$ wherein R$^5$ and R$^6$ are independently selected from the group consisting of hydrogen, alkyl, substituted alkyl, aryl, substituted aryl, aryl alkyl, substituted aryl alkyl, heteroaryl, and substituted heteroaryl; and q is an integer of from 1 to 10, and preferably, from 1 to 4.

In one embodiment, the photocleavable linking groups have the formula:

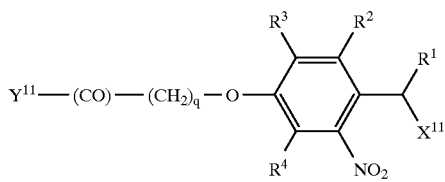

wherein, $R^1$ is hydrogen, $C_1$–$C_8$ alkyl; $R^2$ and $R^4$ are each independently hydrogen, $C_1$–$C_8$ alkyl or $C_1$–$C_8$ alkoxy; $R^3$ is $C_1$–$C_8$ alkoxy; $X^{11}$ and $Y^{11}$ are each independently selected from the group consisting of —Br, —Cl, —OH, —OP, —NH$_2$, —NHP, in which P is a suitable protecting or activating group, and —NR$^5$R$^6$ wherein R$^5$ and R$^6$ are independently selected from the group consisting of hydrogen, alkyl, substituted alkyl, aryl, substituted aryl, aryl alkyl, substituted aryl alkyl, heteroaryl, and substituted heteroaryl ; and q is an integer of from 1 to 4. Preferably, $R^1$ is hydrogen or methyl, $R^2$ and $R^4$ are both hydrogen, $R^3$ is methoxy, $Y^{11}$ is OH, and $X^{11}$ is —Br, —OH, —O(CO)Cl, —OCH$_2$Cl, —O(CO)OAr, —OAc, —NH$_2$, —ODMT, —NHBOC, —NHAc, or —NHFmoc.

In another embodiment, the photocleavable linking groups have the formula:

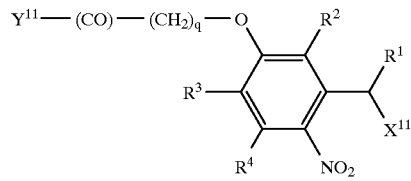

wherein, $R^1$ is hydrogen, $C_1$–$C_8$ alkyl; $R^2$ and $R^4$ are each independently hydrogen, $C_1$–$C_8$ alkyl or $C_1$–$C_8$ alkoxy; $R^3$ is $C_1$–$C_8$ alkoxy; $X^{11}$ and $Y^{11}$ are each independently selected from the group consisting of —Br, —Cl, —OH, —NH$_2$, —OP, —NHP, in which P is a suitable protecting or activating group, and —NR$^5$R$^6$ wherein R$^5$ and R$^6$ are independently selected from the group consisting of hydrogen, alkyl, substituted alkyl, aryl, substituted aryl, aryl alkyl, substituted aryl alkyl, heteroaryl, and substituted heteroaryl; and q is an integer of from 1 to 4. Preferably, $R^1$ is hydrogen or methyl, $R^2$ and $R^4$ are both hydrogen, $R^3$ is methoxy, $Y^{11}$ is —OH, and $X^{11}$ is —Br, —OH, —O(CO)Cl, —OCH$_2$Cl, —O(CO)OAr, —OAc, —NH$_2$, —ODMT, —NHBOC —NHAc, or —NHFmoc.

Particularly preferred photocleavable protecting groups are:

wherein $R^1$, $R^2$ and $R^4$ are hydrogen, $R^3$ is methoxy, $Y^{11}$ is —OH, and $X^{11}$ is —Br, and q is 1;

wherein $R^1$, $R^2$ and $R^4$ are hydrogen, $R^3$ is methoxy, $Y^{11}$ is —OH, and $X^{11}$ is —Br, and q is 3;

wherein $R^1$, $R^2$ and $R^4$ are hydrogen, $R^3$ is methoxy, $Y^{11}$ is —OH, and $X^{11}$ is —OH, and q is 1;

wherein $R^1$, $R^2$ and $R^4$ are hydrogen, $R^3$ is methoxy, $Y^{11}$ is —OH, and $X^{11}$ is —OH, and q is 3;

wherein $R^1$, $R^2$ and $R^4$ are hydrogen, $R^3$ is methoxy, $Y^{11}$ is —OH, and $X^{11}$ is —OAc, and q is 1;

wherein $R^1$, $R^2$ and $R^4$ are hydrogen, $R^3$ is methoxy, $Y^{11}$ is —OH, and $X^{11}$ is —OAc, and q is 3;

wherein $R^1$, $R^2$ and $R^4$ are hydrogen, $R^3$ is methoxy, $Y^{11}$ is —OH, and $X^{11}$ is —NH$_2$, and q is 1;

wherein $R^1$, $R^2$ and $R^4$ are hydrogen, $R^3$ is methoxy, $Y^{11}$ is —OH, and $X^{11}$ is —NH$_2$, and q is 3;

wherein $R^1$, $R^2$ and $R^4$ are hydrogen, $R^3$ is methoxy, $Y^{11}$ is —OH, and $X^{11}$ is —NAc, and q is 1;

wherein $R^1$, $R^2$ and $R^4$ are hydrogen, $R^3$ is methoxy, $Y^{11}$ is —OH, and $X^{11}$ is —NAc, and q is 3;

wherein $R^1$, $R^2$ and $R^4$ are hydrogen, $R^3$ is methoxy, $Y^{11}$ is —OH, and $X^{11}$ is —NHFmoc, and q is 1;

wherein $R^1$, $R^2$ and $R^4$ are hydrogen, $R^3$ is methoxy, $Y^{11}$ is —OH, and $X^{11}$ is —NHFmoc, and q is 3;

wherein $R^1$, $R^2$ and $R^4$ are hydrogen, $R^3$ is methoxy, $Y^{11}$ is —OH, and $X^{11}$ is —O(CO)Cl, and q is 1;

wherein $R^1$, $R^2$ and $R^4$ are hydrogen, $R^3$ is methoxy, $Y^{11}$ is —OH, and $X^{11}$ is —O(CO)Cl, and q is 3;

wherein $R^1$, $R^2$ and $R^4$ are hydrogen, $R^3$ is methoxy, $Y^{11}$ is —OH, and $X^{11}$ is —OCH$_2$Cl, and q is 1;

wherein $R^1$, $R^2$ and $R^4$ are hydrogen, $R^3$ is methoxy, $Y^{11}$ is —OH, and $X^{11}$ is —OCH$_2$Cl, and q is 3;

wherein $R^1$ is methyl, $R^2$ and $R^4$ are hydrogen, $R^3$ is methoxy, $Y^{11}$ is —OH, and $X^{11}$ is —Br, and q is 1;

wherein R¹ is methyl, R² and R⁴ are hydrogen, R³ is methoxy, Y¹¹ is —OH, and X¹¹ is —Br, and q is 3;

wherein R¹ is methyl, R² and R⁴ are hydrogen, R³ is methoxy, Y¹¹ is —OH, and X¹¹ is —OH, and q is 1;

wherein R¹ is methyl, R² and R⁴ are hydrogen, R³ is methoxy, Y¹¹ is —OH, and X¹¹ is —OH, and q is 3;

wherein R¹ is methyl, R² and R⁴ are hydrogen, R³ is methoxy, Y¹¹ is —OH, and X¹¹ is —OAc, and q is 1;

wherein R¹ is methyl, R² and R⁴ are hydrogen, R³ is methoxy, Y¹¹ is —OH, and X¹¹ is —OAc, and q is 3;

wherein R¹ is methyl, R² and R⁴ are hydrogen, R³ is methoxy, Y¹¹ is —OH, and X¹¹ is —NH₂, and q is 1;

wherein R¹ is methyl, R² and R⁴ are hydrogen, R³ is methoxy, Y¹¹ is —OH, and X¹¹ is —NH₂, and q is 3;

wherein R¹ is methyl, R² and R⁴ are hydrogen, R³ is methoxy, Y¹¹ is —OH, and X¹¹ is —NAc, and q is 1;

wherein R¹ is methyl, R² and R⁴ are hydrogen, R³ is methoxy, Y¹¹ is —OH, and X¹¹ is —NAc, and q is 3;

wherein R¹ is methyl, R² and R⁴ are hydrogen, R³ is methoxy, Y¹¹ is —OH, and X¹¹ is —NHFmoc, and q is 1;

wherein R¹ is methyl, R² and R⁴ are hydrogen, R³ is methoxy, Y¹¹ is —OH, and X¹¹ is —NHFmoc, and q is 3;

wherein R¹ is methyl, R² and R⁴ are hydrogen, R³ is methoxy, Y¹¹ is —OH, and X¹¹ is —O(CO)Cl, and q is 1;

wherein R¹ is methyl, R² and R⁴ are hydrogen, R³ is methoxy, Y¹¹ is —OH, and X¹¹ is —O(CO)Cl, and q is 3;

wherein R¹ is methyl, R² and R⁴ are hydrogen, R³ is methoxy, Y¹¹ is —OH, and X¹¹ is —OCH₂Cl, and q is 1; or wherein R¹ is methyl, R² and R⁴ are hydrogen, R³ is methoxy, Y¹¹ is —OH, and X¹¹ is —OCH₂Cl, and q is 3.

Although these compounds are shown with specific protecting groups, one of skill in the art will readily appreciate that any suitable amrine, hydroxy, or carboxy protecting group can be used.

According to another embodiment of this invention, the photocleavable protecting groups of this invention are incorporated into a composition having the formula:

A—B—L wherein A is a solid substrate, B is a valence bond or a derivatizing group, and L is a photocleavable linking group having the formula:

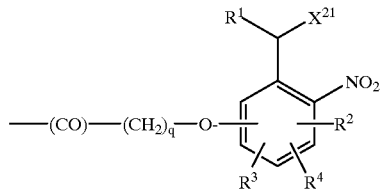

wherein,

R¹ is hydrogen, C₁–C₈ alkyl, aryl or arylalkyl; R², R³ and R⁴ are each independently hydrogen, C₁–C₈ alkyl, or C₁–C₈ alkoxy; X²¹ is halogen, —SH, —SP, —OH, —NH₂, —OP or —NHP, wherein P is a suitable protecting or activating group; and q is an integer of from 1 to 10. One of skill in the art will readily appreciate that these radicals L are derivatives of the photocleavable linking groups shown above. Preferably, the derivatizing group comprises an amino acid, peptide, or polyether chain having an amine functionality at the termini. More preferably, the derivatizing group will comprise —NH—(CH₂CH₂O)ₙCH₂CH₂NH—, —NH—CH₂(CH₂CH₂O)ₙ—CH₂CH₂CH₂NH—, —NH—CH₂(CH₂CH₂CH₂O)ₙCH₂CH₂CH₂NH— or —NH—(CH₂)ₘO(CH₂)ₙO(CH₂)ₘNH—, in which n is an integer of from 1 to 10 and m is an integer of from 1 to 6. In a particularly preferred embodiment, the derivatizing group is —NH—(CH₂CH₂O)₂CH₂CH₂NH—.

Yet another embodiment of this invention provides for methods for utilizing the photocleavable linkers and compositions described above in methods of synthesizing small molecule ligands and peptides, and libraries thereof.

A further understanding of the nature and advantages of the inventions herein may be realized by reference to the remaining portions of the specification and the attached drawings.

BRIEF DESCRIPTION OF THE DRAWINGS

FIG. 2 illustrates the results achieved by removal of two thiazolidinones from a resin via photolysis. The thiazolidinones were synthesized on a resin having a photocleavable linking group.

FIG. 3 shows the HPLC chromatogram of the resulting soluble peptide and illustrates the purity of each. The principle peak at 18.3 min. comigrated with authentic CCK peptide and its identity was also confirmed by mass spectroscopy.

DESCRIPTION OF THE PREFERRED EMBODIMENT

I. Terminology

Figure 1:
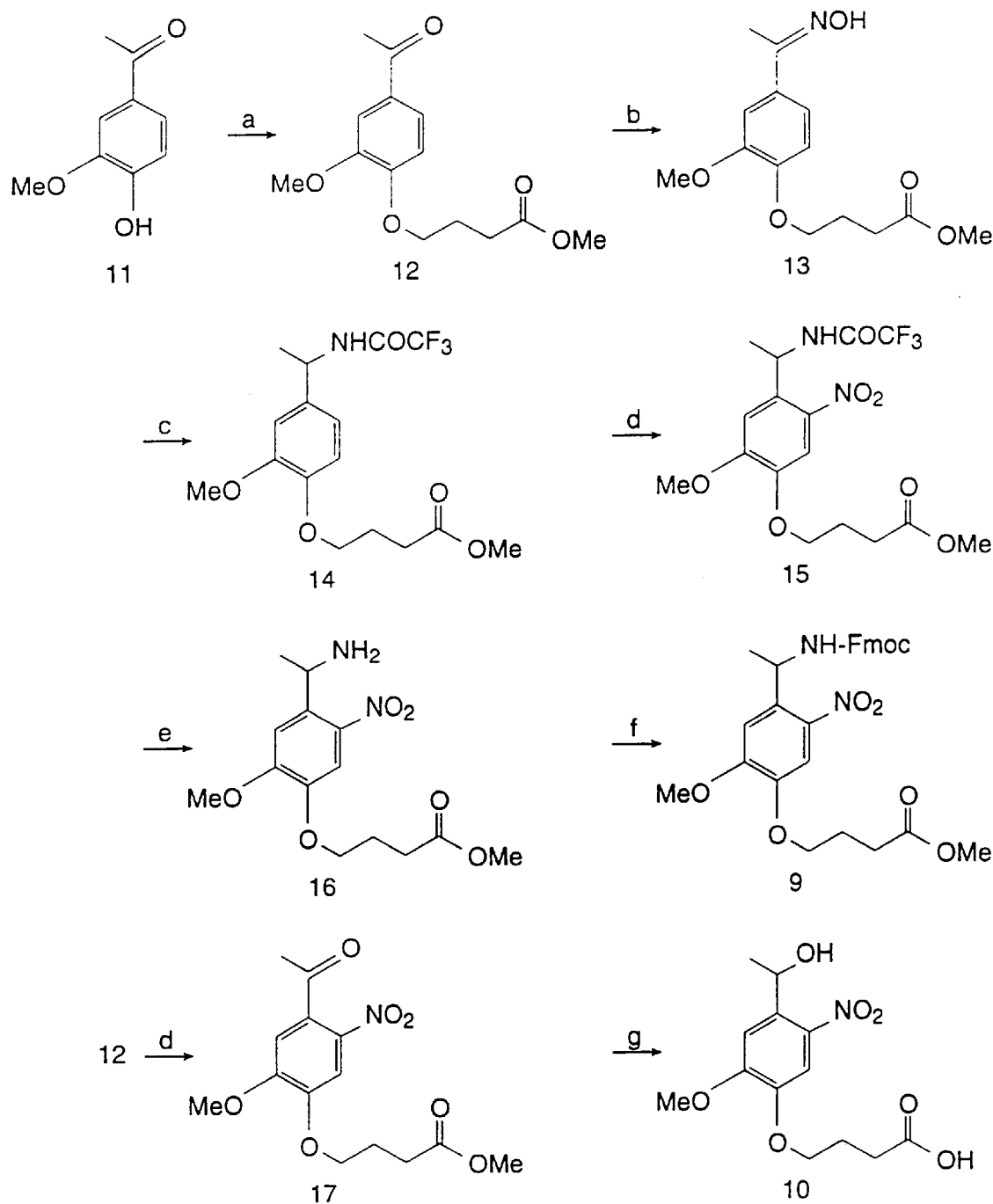
FIG. 1 illustrates a reaction scheme for the preparation of preferred photocleavable linkers, Compounds 9 and 10.
Figure 2A:
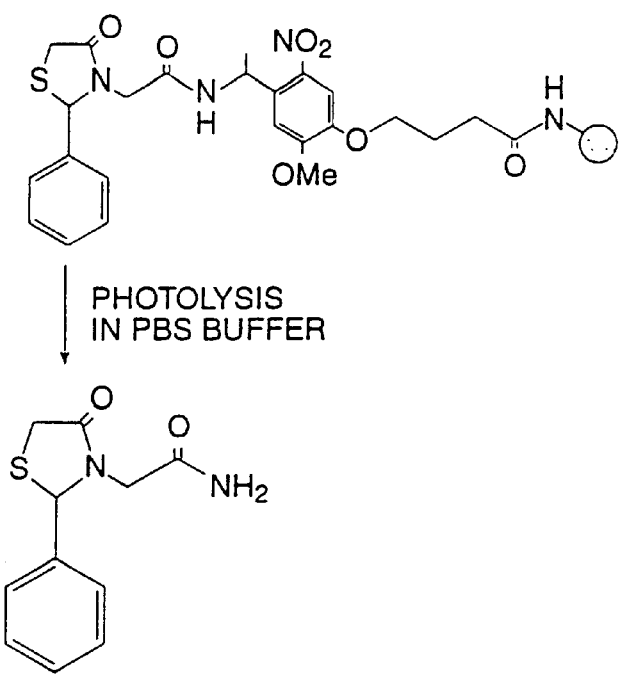
FIGS. 2A and 2B show the reactions which produce the two thiazolidinones.
Figure 2B:
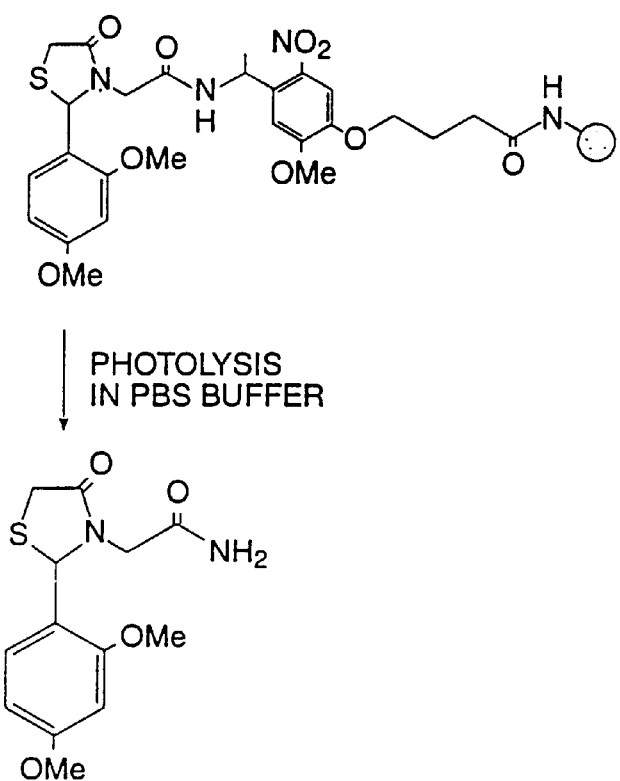
Figure 2C:
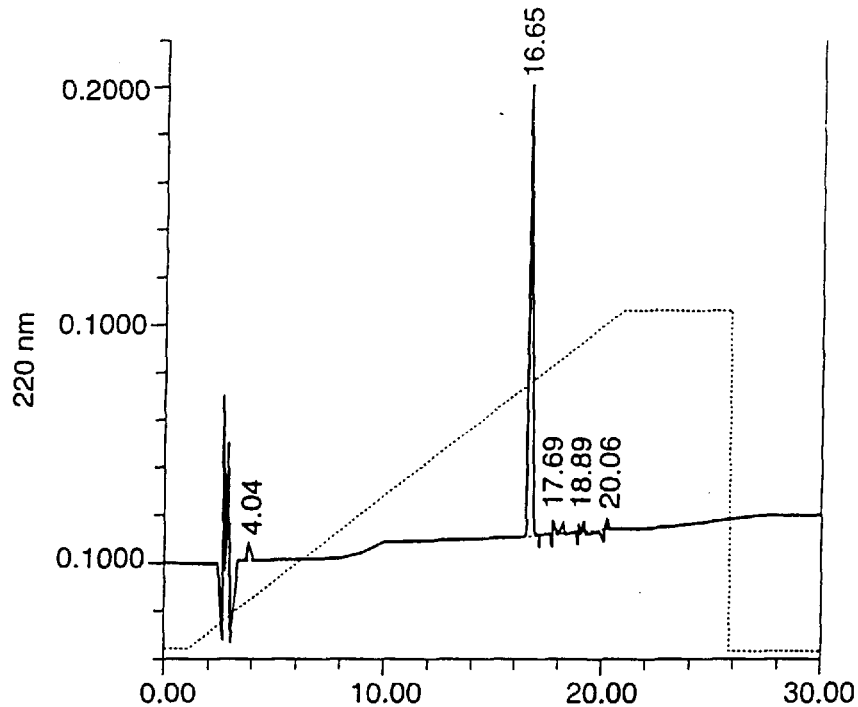
FIGS. 2C and 2D show the HPLC chromatograms of the resulting thiazolidinones and illustrate the purity of each.
Figure 2D:
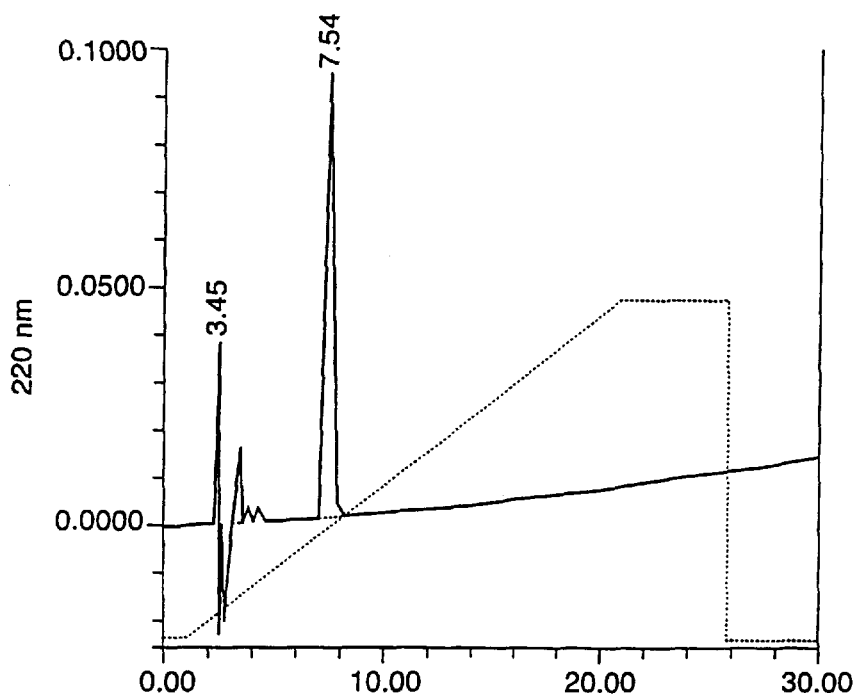

Unless otherwise stated, the following terms used in the specification and claims have the meanings given below:

Chemical terms

"Activating group" refers to those groups which, when attached to a particular functional group or reactive site, render that site more reactive toward covalent bond formation with a second functional group or reactive site. For example, the group of activating groups which can be used in the place of a hydroxyl group include —O(CO)Cl; —OCH₂Cl; —O(CO)OAr, where Ar is an aromatic group, preferably, a p-nitrophenyl group; —O(CO)(ONHS); and the like. The group of activating groups which are useful for a carboxylic acid include simple ester groups and anhydrides. The ester groups include alkyl, aryl and alkenyl esters and in particular such groups as 4-nitrophenyl, N-hydroxylsuccinimide and pentafluorophenol. Other activating groups are known to those of skill in the art.

"Alkoxy" refers to the group alkyl—O—.

"Alkyl" refers to a cyclic, branched, or straight chain chemical group containing only carbon and hydrogen, such as methyl, heptyl, —(CH$_2$)$_2$—, and adamantyl. Alkyl groups can either be unsubstituted or substituted with one or more substituents, e.g., halogen, alkoxy, acyloxy, amino, aryl, hydroxyl, mercapto, carboxy, benzyloxy, phenyl, benzyl, or other functionality which may be suitably blocked, if necessary for purposes of the invention, with a protecting group. When "alkyl" or "alkylene" is used to refer to a linking group or a spacer, it is taken to be a group having two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$)$_2$CH$_2$—. Preferred alkyl groups as substituents are those containing 1 to 10 carbon atoms, with those containing 1 to 6 carbon atoms being particularly preferred. Preferred alkyl or alkylene groups as linking groups are those containing 1 to 20 carbon atoms, with those containing 3 to 6 carbon atoms being particularly preferred.

"Amino" or "amine group" refers to the group —NR'R", where R' and R" are independently selected from the group consisting of hydrogen, alkyl, substituted alkyl, aryl, substituted aryl, aryl alkyl, substituted aryl alkyl, heteroaryl, and substituted heteroaryl. In a primary amino group, both R' and R" are hydrogen, whereas in a secondary amino group, either, but not both, R' or R" is hydrogen.

An "α-amino acid" consists of a carbon atom, called the α-carbon, to which is bonded an amino group and a carboxyl group. Typically, this α-carbon atom is also bonded to a hydrogen atom and a distinctive group referred to as a "side chain." The hydrogen atom may also be replaced with a group such as alkyl, substituted alkyl, aryl, substituted aryl, heteroaryl, and other groups. The side chains of naturally occurring amino acids are well known in the art and include, for example, hydrogen (as in glycine), alkyl (as in alanine (methyl), valine (isopropyl), leucine (sec-butyl), isoleucine (iso-butyl), and proline (—(CH$_2$)$_3$—)), substituted alkyl (as in serine (hydroxymethyl), cysteine (thiomethyl), aspartic acid (carboxymethyl), asparagine, arginine, glutamine, glutamic acid, and lysine), aryl alkyl (as in phenylalanine, histidine, and tryptophan), substituted aryl alkyl (as in tyrosine and thyroxine), and heteroaryl (as in histidine). See, e.g., Harper et al. (1977) *Review of Physiological Chemistry,* 16th Ed., Lange Medical Publications, pp. 21–24.

In addition to naturally occurring side chains, the amino acids used in the present invention may possess synthetic side chains. A "synthetic side chain" is any side chain not found in a naturally occurring amino acid. For example, a synthetic side chain can be an isostere of the side chain of a naturally occurring amino acid. Naturally occurring and synthetic side chains may contain reactive functionalities, such as hydroxyl, mercapto, and carboxy groups. One skilled in the art will appreciate that these groups may have to be protected to carry out the desired reaction scheme. As stated above, the hydrogen at the α-carbon can also be replaced with other groups; those of skill in the art recognize the medicinal importance of α-methyl amino acids and other α-, α-disubstituted amino acids.

"Protected amino acid" refers to an amino acid, typically an α-amino acid having either or both the amine functionality and the carboxylic acid functionality suitably protected by one of the groups described above. Additionally, for those amino acids having reactive sites or functional groups on a side chain (i.e., serine, tyrosine, glutamic acid), the term "protected amino acid" is meant to refer to those compounds which optionally have the side chain functionality protected as well.

"Aryl" or "Ar" refers an aromatic substituent which may be a single ring or multiple rings which are fused together, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aryl moieties may also be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

"Aryloxy" refers to the group aryl—O— or heteroaryl—O—.

"Arylalkyl" or "aralkyl" refers to the groups R'—Ar and R—HetAr, where Ar is an aryl group, HetAr is a heteroaryl group, and R' is straight-chain or branched-chain aliphatic group (for example, benzyl, phenylethyl, 3-(4-nitrophenyl)propyl, and the like). Preferred aryl groups include phenyl, 1-naphthyl, 2-naphthyl, biphenyl, phenylcarboxylphenyl (i.e., derived from benzophenone), and the like.

"Carboxy" or "carboxyl" refers to the group —R'(COOH) where R' is alkyl, substituted alkyl, aryl, substituted aryl, aryl alkyl, substituted aryl alkyl, heterocyclic, heteroaryl, or substituted heteroaryl.

"Carboxyalkyl" refers to the group —(CO)—R' where R' is alkyl or substituted alkyl.

"Carboxyaryl" refers to the group —(CO)—R' where R' is aryl, heteroaryl, or substutited aryl or heteroaryl.

"Chemical library" or "array" is an intentionally created collection of differing molecules which can be prepared either synthetically or biosynthetically and screened for biological activity in a variety of different formats (e.g., libraries of soluble molecules; and libraries of compounds tethered to resin beads, silica chips, or other solid supports). The term is also intended to refer to an intentionally created collection of stereoisomers.

"Combinatorial synthesis strategy" or "combinatorial chemistry" refers to an ordered strategy for the parallel synthesis of diverse compounds by sequential addition of reagents which leads to the generation of large chemical libraries. Thus, combinatorial chemistry refers to the systematic and repetitive, covalent connection of a set of different "building blocks" of varying structures to each other to yield large arrays of diverse molecular entities.

"Linker" refers to a molecule or group of molecules attached to a solid support and spacing a synthesized compound from the solid support, such as for exposure/binding to a receptor.

"Polyethylene glycol" refers to those molecules which have repeating units of ethylene glycol, for example, hexaethylene glycol (HO—(CH$_2$CH$_2$O)$_5$—CH$_2$CH$_2$OH). When the term "polyethylene glycol" is used to refer to linking groups and spacer groups, it would be understood by one of skill in the art that other polyethers or polyols could be used as well (i.e, polypropylene glycol or mixtures of ethylene and propylene glycols).

"Predefined region" refers to a localized area on a solid support which is, was, or is intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct compound is synthesized is smaller than about 1 cm$^2$ or less than 1 mm$^2$. Within these regions, the molecule synthesized therein is preferably synthesized in a substantially pure form. In additional embodiments, a predefined region can be achieved by physically separating the regions (i.e., beads, resins, gels, etc.) into wells, trays, etc.

"Protecting group" refers to a chemical group that exhibits the following characteristics: (1) reacts selectively with the desired functionality in good yield to give a derivative that is stable to the projected reactions for which protection is desired; 2) can be selectively removed from the derivatized solid support to yield the desired functionality; and 3) is removable in good yield by reagents compatible with the other functional group(s) generated in such projected reactions. Examples of protecting groups can be found in Greene et al. (1991) *Protective Groups in Organic Synthesis*, 2nd Ed. (John Wiley & Sons, Inc., New York). Preferred protecting groups include photolabile protecting groups (such as methylnitropiperonyloxycarbonyl (Menpoc), methylnitropiperonyl (Menp), nitroveratryl (Nv), nitroveratryloxycarbonyl (Nvoc), or nitroveratryloxymethyl ether (Nvom)); acid-labile protecting group (such as Boc or DMT); base-labile protecting groups (such as Fmoc, Fm, phosphonioethoxycarbonyl (Peoc, see Kunz (1976) *Chem. Ber.* 109: 2670); groups which may be removed under neutral conditions (e.g., metal ion-assisted hydrolysis ), such as DBMB (see Chattopadhyaya et al. (1979) *J.C.S. Chem. Comm.* 987–990), allyl or alloc (see, e.g., Greene and Wuts, "Protective Groups in Organic Synthesis", 2nd Ed., John Wiley & Sons, Inc., New York, N.Y. (1991), 2-haloethyl (see Kunz and Buchholz (1981) *Angew. Chem. Int. Ed. Engl.* 20: 894), and groups which may be removed using fluoride ion, such as 2-(trimethylsilyl)ethoxymethyl (SEM), 2-(trimethylsilyl)ethyloxycarbonyl (Teoc) or 2-(trimethylsilyl)ethyl (Te) (see, e.g., Lipshutz et al. (1980) *Tetrahedron Lett.* 21:3343–3346)); and groups which may be removed under mild reducing conditions (e.g., with sodium borohydride or hydrazine), such as Lev. Id. at 30–31, 97, and 112. Particularly preferred protecting groups include Fmoc, Fm, Menpoc, Nvoc, Nv, Boc, CBZ, allyl, alloc, Npeoc (4-nitrophenethyloxycarbonyl) and Npeom (4-nitrophenethyloxy-methyloxy).

"Solid support", "support", and "substrate" refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by references to the examples hereinbelow. However, other equivalent separation or isolation procedures can, of course, also be used.

Ligand

A ligand is a molecule that is recognized by a receptor. Examples of ligands which can be synthesized using the methods and compounds of this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

Receptor

A receptor is a molecule that has an affinity for a ligand. Receptors may be naturally-occurring or manmade molecules. They can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as anti-ligands. As the term receptors is used herein, no difference in meaning is intended. A "Ligand Receptor Pair" is formed when two molecules have combined through molecular recognition to form a complex.

Specific examples of receptors which can be investigated using ligands and libraries prepared using the methods and compounds of this invention include but are not restricted to:

a) Microorganism receptors: Determination of ligands that bind to microorganism receptors such as specific transport proteins or enzymes essential to survival of microorganisms would be a useful tool for discovering new classes of antibiotics. Of particular value would be antibiotics against opportunistic fungi, protozoa, and bacteria resistant to antibiotics in current use.

b) Enzymes: For instance, a receptor can comprise a binding site of an enzyme such as an enzyme responsible for cleaving a neurotransmitter; determination of ligands for this type of receptor to modulate the action of an enzyme that cleaves a neurotransmitter is useful in developing drugs that can be used in the treatment of disorders of neurotransmission.

c) Antibodies: For instance, the invention may be useful in investigating a receptor that comprises a ligand-binding site on an antibody molecule which combines with an epitope of an antigen of interest; determining a sequence that mimics an antigenic epitope may lead to the development of vaccines in which the immunogen is based on one or more of such sequences or lead to the development of related diagnostic agents or compounds useful in therapeutic treatments such as for autoimmune diseases (e.g., by blocking the binding of the "self" antibodies).

d) Nucleic Acids: Sequences of nucleic acids may be synthesized to establish DNA or RNA binding sequences that act as receptors for synthesized sequence.

e) Catalytic Polypeptides: Polymers, preferably antibodies, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: Determination of the ligands which bind with high affinity to a receptor such as the receptors for insulin and growth hormone is useful in the development of, for example, an oral replacement of the daily injections which diabetics must take to relieve the symptoms of diabetes or a replacement for growth hormone. Other examples of hormone receptors include the vasocontrictive hormone receptors; determination of ligands for these receptors may lead to the development of drugs to control blood pressure.

g) Opiate receptors: Determination of ligands which bind to the opiate receptors in the brain is useful in the development of less-addictive replacements for morphine and related drugs.

Channel Block

A material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

Abbreviations: The following abbreviations are intended to have the following meanings:

Boc=t-butyloxycarbonyl
BOP=benzotriazol-1-yloxytris(dimethylamino) phosphonium hexafluorophosphate
DCC=dicyclohexylcarbodiimide
Ddz=dimethoxydimethylbenzyloxy
DIC=diisopropylcarbodiimide
DMT=dimethoxytrityl
Fmoc=fluorenylmethyloxycarbonyl
HBTU=2-(1H-benzotriazol-1-yl)-1,1,3,3-tetramethyluronium hexafluorophosphate
HOBt=1-hydroxybenzotriazole
Menpoc=methylnitropiperonyloxycarbonyl
Menp=methylnitropiperonyl
Nv=nitroveratryl
Nvoc=6-nitroveratryloxycarbonyl and other photoremovable groups
OPfp=pentafluorophenyloxy
OSu=N-succinimidyloxy (also known as NHS)
PG=protective group
TFA=trifluoroacetic acid II. General The present invention provides novel compounds which are useful as photochemically cleavable linking groups which can be represented by the formula:

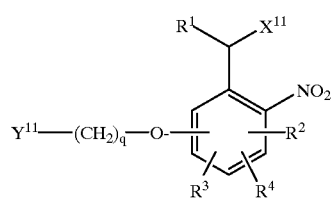

in which $R^1$ is hydrogen, $C_1$–$C_8$ alkyl, aryl or arylalkyl; $R^2$, $R^3$ and $R^4$ are each independently hydrogen, $C_1$–$C_8$ alkyl, or $C_1$–$C_8$ alkoxy; $X^{11}$ and $Y^{11}$ are each independently halogen, —SH, —SP, —OH, —OP, —NH$_2$, —NHP, in which P is a suitable protecting or activating group, and —NR$^5$R$^6$ wherein R$^5$ and R$^6$ are independently selected from the group consisting of hydrogen, alkyl, substituted alkyl, aryl, substituted aryl, aryl alkyl, substituted aryl alkyl, heteroaryl, and substituted heteroaryl; and q is an integer of from 1 to 10, preferably from 1 to 4.

In one group of embodiments, the compounds are represented by the formula:

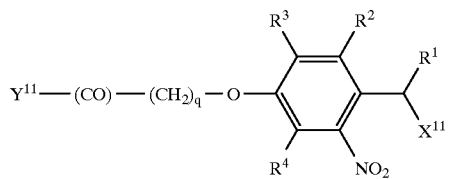

in which $R^1$ is hydrogen, $C_1$–$C_8$ alkyl; $R^2$ and $R^4$ are each independently hydrogen, $C_1$–$C_8$ alkyl or $C_1$–$C_8$ alkoxy; $R^3$ is $C_1$–$C_8$ alkoxy; $X^{11}$ and $Y^{11}$ are each independently —Br, —Cl, —OH, —NH$_2$, —OP, —NHP, in which P is a suitable protecting or activating group, and —NR$^5$R$^6$ wherein R$^5$ and R$^6$ are independently selected from the group consisting of hydrogen, alkyl, substituted alkyl, aryl, substituted aryl, aryl alkyl, substituted aryl alkyl, heteroaryl, and substituted heteroaryl; and q is an integer of from 1 to 4. In particularly preferred embodiments, $R^1$ is hydrogen or methyl, $R^2$ and $R^4$ are both hydrogen, $R^3$ is methoxy, $Y^{11}$ is —OH, and $X^{11}$ is —Br, —OH, —O(CO)Cl, —OCH$_2$Cl, —O(CO)OAr, —OAc, —NH$_2$, —ODMT, —NHBOC, —NHAc, or —NHFmoc.

In another group of embodiments, the compounds are represented by the formula:

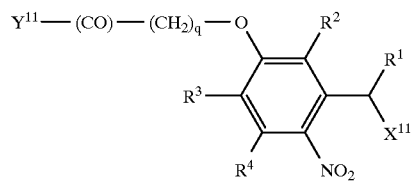

in which the symbols $R^1$, $R^2$, $R^3$, $R^4$, $X^{11}$, $Y^{11}$ and q represent those groups described above for the first group of embodiments. As above, embodiments which are particularly preferred are those in which $R^1$ is methyl, $R^2$ and $R^4$ are both hydrogen, $R^3$ is methoxy, $Y^{11}$ is —OH, and $X^{11}$ is —Br, —OH, —O(CO)Cl, —OCH$_2$Cl, —O(CO)OAr, —OAc, —NH$_2$, —ODMT, —NHBOC —NHAc, or —NHFmoc.

Exemplary of the photochemically cleavable linking groups of the present invention are structures 3–6, below.

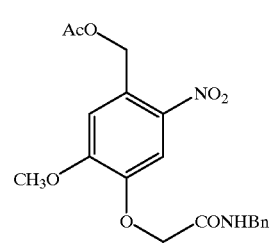

3

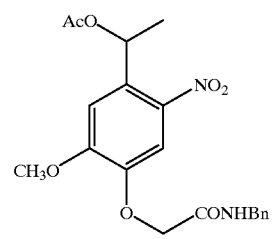

4

-continued

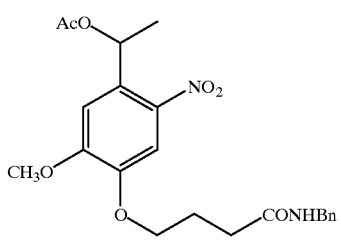

5

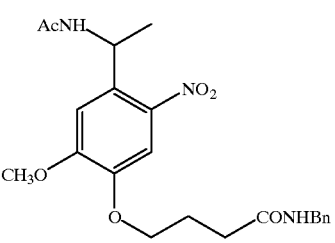

6

Although Compounds 3–6 are illustrated with an amide linkage (—CONHBn) on one terminus and an ester (for example, —OAc) or amide (for example, —NHAc) linkage on the other terminus, one of skill in the art will appreciate that these photochemically cleavable linking groups can be prepared, stored, and in some embodiments, utilized in their unprotected forms as the corresponding free adds, free amines, and/or free hydroxyl compounds, or salts thereof. In addition, protecting group other than the exemplified Ac— and Bn— groups can also be used. The choice of protecting group will depend on the nature of subsequent couplings and will be readily apparent to one of skill in the art.

These compounds which are suitable as photochemically cleavable linking groups can be prepared by standard synthetic methods known to those of skill in the art. For example, linking group 3 can be prepared from commercially available vanillin (Aldrich Chemical Company, Milwaukee, Wis., USA). Alkylation of the hydroxyl functionality of vanillin with t-butyl bromoacetate provides a phenoxyacetic ester derivative which can be nitrated using nitric acid. The carboxylic acid functionality which is formed via ester cleavage during the nitration process can be converted to the benzamide using standard methods. Reduction of the aldehyde with sodium borohydride followed by acylation of the hydroxyl group thus formed with acetic anhydride provides linking group 3.

Preparation of linking group 4 can be achieved in a similar sequence of steps beginning with acetovallinone (Aldrich Chemical Company). Preparation of linking group 5 can be achieved using methods similar to those employed for linking group 4, by substituting t-butyl 4-bromobutyrate for t-butyl bromoacetate. Preparation of 6 can be achieved by reductive amination of the keto-acid intermediate used in the preparation of 5. Following amination, the resultant amine is protected as its acetamide and the carboxylic acid functionality is converted to a benzamide to provide 6.

Linking groups similar to 3, 4 and 5, but having —NH—P, wherein P is a suitable protecting group (as exemplified with a Fmoc group below) in place of —OAc can also be prepared using known methods. For example, the aldehyde-acid formed in the preparation of 3 can be treated under reductive amination conditions to provide an aminomethyl substituent in place of the aldehyde functionality. Protection of the amine with Fmoc-Cl can be carried out according to known procedures to provide linking group 7. Similarly, 8 can be prepared via reductive amination of the keto-acid prepared in the synthesis of 4, followed by amino group protection with Fmoc-Cl. Other protecting groups which are also suitable include, for example, ALLOC and BOC.

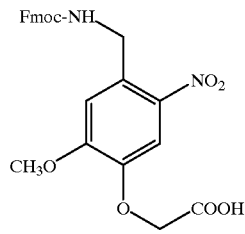

7

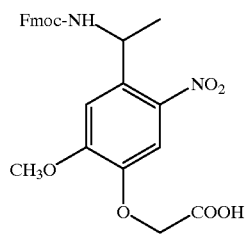

8

Likewise, analogs of compound 5 can be readily prepared, as shown in FIG. 1. The linker can be prepared with the Fmoc protecting group through a seven step sequence starting with acetovanillone. Of particular note is that the procedure typically does not require any chromatography. All intermediates in this scheme generally are crystalline and the reaction sequence can be carried out in preparative scale to afford ample quantities of the linker in roughly 55% overall yield. See Holmes et al. (1995) *J. Org. Chem.* 60: 2318–9. Alternative protecting group strategies in addition to Fmoc are also accessible for all of the above described linkers, for example, by derivatizing intermediate 16 with other common amine protecting groups.

In another aspect, the present invention provides compositions which are solid substrates derivatized with the compounds of the present invention. These substrates having "photochemically cleavable" linking groups just described, can be represented by the formula:

A—B—L in which A is a solid substrate, B is a bond or a derivatizing group and L is a linking group and will find use particularly in the solid phase synthesis of small molecule ligands and peptides, and libraries thereof.

The solid substrate or solid support may be of any shape, although they preferably will be roughly spherical. The supports need not necessarily be homogenous in size, shape or composition; although the supports usually and preferably will be uniform. In some embodiments, supports that are very uniform in size may be particularly preferrd. In another embodiment, two or more distinctly different populations of solid supports may be used for certain purposes.

Solid supports may consist of many materials, limited primarily by capacity for derivatization to attach any of a number of chemically reactive groups and compatibility with the synthetic chemistry used to produce the array and, in some embodiments the methods used for tag attachment and/or synthesis. Suitable support materials typically will be the type of material commonly used in peptide and polymer synthesis and include glass, latex, polyethylene glycol, heavily cross-linked polystyrene or similar polymers, gold or other colloidal metal particles, and other materials known to those skilled in the art. Except as otherwise noted, the chemically reactive groups with which such solid supports may be derivatized are those commonly used for solid phase synthesis of the polymer and thus will be well known to those skilled in the art, i.e., carboxyls, amines and hydroxyls.

To improve washing efficiencies, one can employ nonporous supports or other solid supports less porous than typical peptide synthesis supports; however, for certain applications of the invention, quite porous beads, resins, or other supports work well and are often preferable. A preferred support is resin, such as the beads described in co-pending U.S. Pat. No. 5,770,358. In general, the bead size is in the range of 1 nm to 100 μm, but a more massive solid support of up to 1 mm in size may sometimes be used. Particularly preferred resins include Sasrin resin (a polystyrene resin available from Bachem Bioscience, Switzerland); and TentaGel S AC, TentaGel PHB, or TentaGel S $NH_2$ resin (polystyrene-polyethylene glycol copolymer resins available from Rappe Polymere, Tubingen, Germany). Other preferred supports are commercially available and described by Novabiochem, La Jolla, Calif.

In other embodiments, the solid substrate is flat, or alternatively, may take on alternative surface configurations. For example, the solid substrate may contain raised or depressed regions on which synthesis takes place. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid substrate materials will be readily apparent to those of skill in the art. Preferably, the surface of the solid substrate will contain reactive groups, which could be carboxyl, amino, hydroxyl, thiol, or the like. More preferably, the surface will be optically transparent and will have surface Si—OH functionalities, such as are found on silica surfaces.

According to the present embodiment, when bound to a solid support, the photocleavable linker is attached by means of a derivatizing group "B". One can, of course, incorporate a wide variety of derivatizing groups, depending upon the application and the effect desired. For instance, one can select derivatizing groups that impart hydrophobicity, hydrophilicity, or steric bulk to achieve desired effects on properties such as coupling or binding efficiency. In one aspect of the invention, the derivatizing group will comprise an amino acid or peptide. For example, branched derivatizing groups, i.e., derivatizing groups with bulky side chains such as the derivatizing group, Fmoc-Thr(tBu), are used to provide rigidity to or to control spacing of the molecules on the solid support in a library or between a molecule and a tag in the library. Particularly preferred derivatizing groups derived from amino acids or peptides include T, EGEGET, and SVT.

In some embodiments, cleavable linkers will be used to facilitate an assay or detection step. Specifically, the advent of methods for the synthesis of diverse chemical compounds on solid supports has resulted in the genesis of a multitude of diagnostic applications for such chemical libraries. A number of these diagnostic applications involve contacting a sample with a solid support, or chip, having multiple attached biological polymers such as peptides and oligonucleotides, or other small ligand molecules synthesized from building blocks in a stepwise fashion, in order to identify any species which specifically binds to one or more of the attached polymers or small ligand molecules. For example, the use of VLSIPS and ESL technologies, disclosed in U.S Pat. Nos. 5,143,854, 5,770,358 and 5,639,603, and incorporated herein by reference for all purposes, and other synthesis and screening methodologies often requires that the support used to assemble the ligands also be used to display the ligands for biological binding experiments. As a result, any linking groups used in preparation of the ligands must perform well in the organic environment used in synthesizing the ligands as well as the aqueous environment typically used in binding assays. By changing the particular derivatizing group and the resulting hydrophilic/hydrophobic properties of the compositions claimed herein, often the presentation of a ligand or peptide to certain receptors, proteins or drugs can be improved.

Prior to attachment to the solid substrate the derivatizing group will have a substrate attaching group at one end, and a reactive site at the other end. The reactive site will be a group which is appropriate for attachment to the photocleavable linking group, L. Groups which are suitable for attachment to a linking group include amine, hydroxyl, thiol, carboxylic acid, ester, amide, isocyanate and isothiocyanate.

Preferably, the derivatizing group is a polymer chain having amine or hydroxyl functional groups at the termini. In one group of preferred embodiments, the derivatizing group comprises an amino acid, peptide, or polyether chain having an amine functionality at the termini. More preferably, the derivatizing group is —NH—$(CH_2CH_2O)_n CH_2CH_2NH$—, —NH—$CH_2(CH_2CH_2O)_n CH_2CH_2CH_2NH$—, —NH—$CH_2 (CH_2CH_2CH_2O)_n CH_2CH_2CH_2NH$— or —NH—$(CH_2)_m O(CH_2)_n$—, $O(CH_2)_m NH$—, in which n is an integer of from 1 to 10 and m is an integer of from 1 to 6. In a particularly preferred embodiment, the derivatizing group is —NH—$(CH_2CH_2O)_2 CH_2CH_2NH$—.

According to the needs of the practitioner, the derivatizing groups can also be combined, for example, by combining an amino acid or peptide derivatizing group with a polymer chain having the appropriate functionality at both termini. Particularly preferred derivatizing groups of this class include $PEG_{15}T$, $PEG_{19}T$, $PEG_{20}T$, $PEG_{24}T$, and $PEG_{30}T$, wherein the polymer chains have the structures shown below:

| Abbreviation | Structure |
| --- | --- |
| $PEG_{15}$ | —NH—$(CH_2CH_2O)_n CH_2CH_2NH$—(CO)$CH_2CH_2CH_2CO$—, where n is 2 |
| $PEG_{19}$ | —NH—$(CH_2)_m O(CH_2)_n O(CH_2)_m NH$—(CO)$CH_2CH_2CH_2CO$—, where m is 3 and n is 4 |
| $PEG_{20}$ | —NH—$CH_2(CH_2CH_2O)_n CH_2CH_2CH_2$—NH—(CO)$CH_2CH_2CH_2CO$—, where n is 3 |
| $PEG_{24}$ | —NH—$(CH_2CH_2O)_n CH_2CH_2NH$—(CO)$CH_2CH_2CH_2CO$—, where n is 5 |
| $PEG_{30}$ | The dimer of $PEG_{15}$ |

Linking groups used in the present compositions which are photochemically cleavable are represented by radicals of the formula:

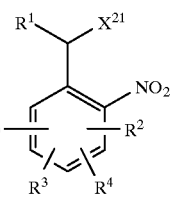

in which $R^1$ is hydrogen, $C_1$–$C_8$ alkyl, aryl or arylalkyl; $R^2$, $R^3$ and $R^4$ are each independently hydrogen, $C_1$–$C_8$ alkyl, or $C_1$–$C_8$ alkoxy; $X^{21}$ is halogen, —SH, —SP, —OH, —NH$_2$, —OP or —NHP, wherein P is a suitable protecting or activating group; and q is an integer of from 1 to 10. One of skill in the art will readily appreciate that these linking groups are analogous to those described above with the replacement of the $Y^{11}$ group by a valence bond or derivatizing group.

In one group of preferred embodiments, L has the formula:

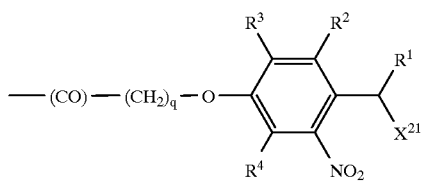

in which $R^1$ is hydrogen, $C_1$–$C_8$ alkyl; $R^2$ and $R^4$ are each independently hydrogen, $C_1$–$C_8$ alkyl or $C_1$–$C_8$ alkoxy; $R^3$ is $C_1$–$C_8$ alkoxy; $X^{21}$ is —Br, —Cl, —OH, —OP, —SH, —SP, —NH$_2$ or —NHP, wherein P is a suitable protecting or activating group; and q is an integer of from 1 to 4. In further preferred embodiments $R^1$ is hydrogen or methyl and $R^3$ is methoxy. More preferably, $R^1$ is methyl, $R^3$ is methoxy, and $R^2$ and $R^4$ are each hydrogen. Still further preferred are those compounds in which n is 3, $R^1$ is methyl, $R^3$ is methoxy, $R^2$ and $R^4$ are each hydrogen, and $X^{21}$ is —OH, —ODMT, —O(CO)Cl, —CH$_2$Cl, —(CO)OAr, —OAc, —NH-Fmoc, —NHAc, or —NH-BOC.

In another group of preferred embodiments, L has the formula:

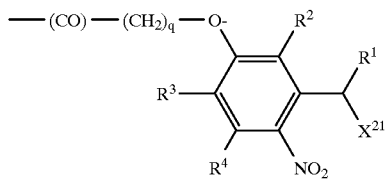

in which the symbols $R^1$, $R^2$, $R^3$, $R^4$, $X^{21}$ and q represent those groups described above for the first group of embodiments. As above, embodiments which are particularly preferred are those in which $R^1$ is methyl and $R^3$ is methoxy. More preferably, $R^1$ is methyl, $R^3$ is methoxy, and $R^2$ and $R^4$ are each hydrogen. Still further preferred are those compounds in which n is 3, $R^1$ is methyl, $R^3$ is methoxy, $R^2$ and $R^4$ are each hydrogen, and $X^{21}$ is —OH, —ODMT, —(CO)Cl, —OCH$_2$Cl, —O(CO)OAr, —OAc, —NH-Fmoc, —NHAc, or —NH-BOC.

The compositions of the present invention can be prepared by standard manipulations of methods already described herein which are well known to those of skill in the art from the diamine derivatives of commercially available polyglycols. For example, hexaethylene glycol (Aldrich Chemical Company, Milwaukee, Wis., USA) can be treated with p-toluenesulfonyl chloride and ammonia to produce a glycol derivative having amino groups at the chain termini. Other methods for the synthesis of the derivatizing group subunit begin with pentaethylene glycol and proceed with a one carbon homologation on each termini via treatment of the diol with p-toluenesulfonyl chloride followed by cyanide ion. Reduction of the resultant dinitrile provides the corresponding diamine. Still other diamines which are useful in the present linking groups are available from Fluka Chemical Co. (Ronkonkoma, N.Y., USA).

III. Use in Synthesis

A. General overview

In yet another aspect, the present invention provides methods for the preparation of small ligand molecules or peptides on a solid support such that the small ligand molecules or peptides are removable from the support upon the application of a suitable energy source. These methods are applicable to the solid phase synthesis of a single molecule or libraries of molecules, as described in greater detail hereinbelow.

In the first step of the present method, a photolabile linking group is attached to a solid support. The photolabile linking group is represented by the formula:

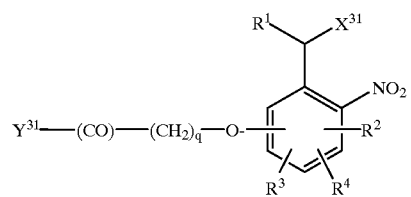

in which $R^1$ is hydrogen, $C_1$–$C_8$ alkyl, aryl or arylalkyl; $R^2$, $R^3$ and $R^4$ are each independently hydrogen, $C_1$–$C_8$ alkyl or $C_1$–$C_8$ alkoxy; $X^{31}$ is halogen, —OH, —OP, —SH, —SP, —NH$_2$ or —NHP and $Y^{31}$ is Br, Cl, OH, NH$_2$, SH, OP, SP and NHP, wherein P is a protecting or activating group; and q is an integer of from 1 to 10. In this step, attachment to the solid support occurs through $Y^{31}$, or alternatively through the carbonyl group attached to $Y^{31}$.

The extent of coupling of the linkers to commercially available amino-supports to afford the corresponding photolabile supports can be determined by conventional Kaiser test. Despite the sensitivity of the supports towards photolytic cleavage, they can be handled without any special precautions other than avoiding direct exposure to sunlight or UV light. The supports can be handled under subdued laboratory lights and stored in foil-wrapped vials.

In an optional second step, protecting groups, where present on $X^{31}$, are removed from the resulting derivatized solid support. In those applications in which a number of diverse small ligand molecules are to be synthesized on the support, the protecting groups may be selectively removed from one region at a time. Methods for this selective removal are described in U.S. Pat. Nos. 5,677,195 and 5,384,261, previously incorporated herein by reference. The removal of protecting groups provides a synthesis initiation site upon which the small ligand molecules can be prepared.

In an optional third step, the synthesis sites on the solid support are activated. For example, a hydroxyl group can be coverted to the corresponding —OP group wherein P is an activating group as defined above. Similarly, amine and carboxyl groups can also be activated using methods known in the art.

In the fourth step of the present method, small ligand molecules or polymers are coupled to the synthesis initiation site. This coupling can involve either the attachment of the entire small ligand molecule or polymer, or it can involve the synthesis of the molecules in a stepwise fashion on the synthesis initiation site. In those embodiments in which the molecules are synthesized in stepwise fashion on the synthesis initiation site, the synthesis can proceed by any of the compatible means discussed under the General Methods section hereinbelow.

Figure 4:
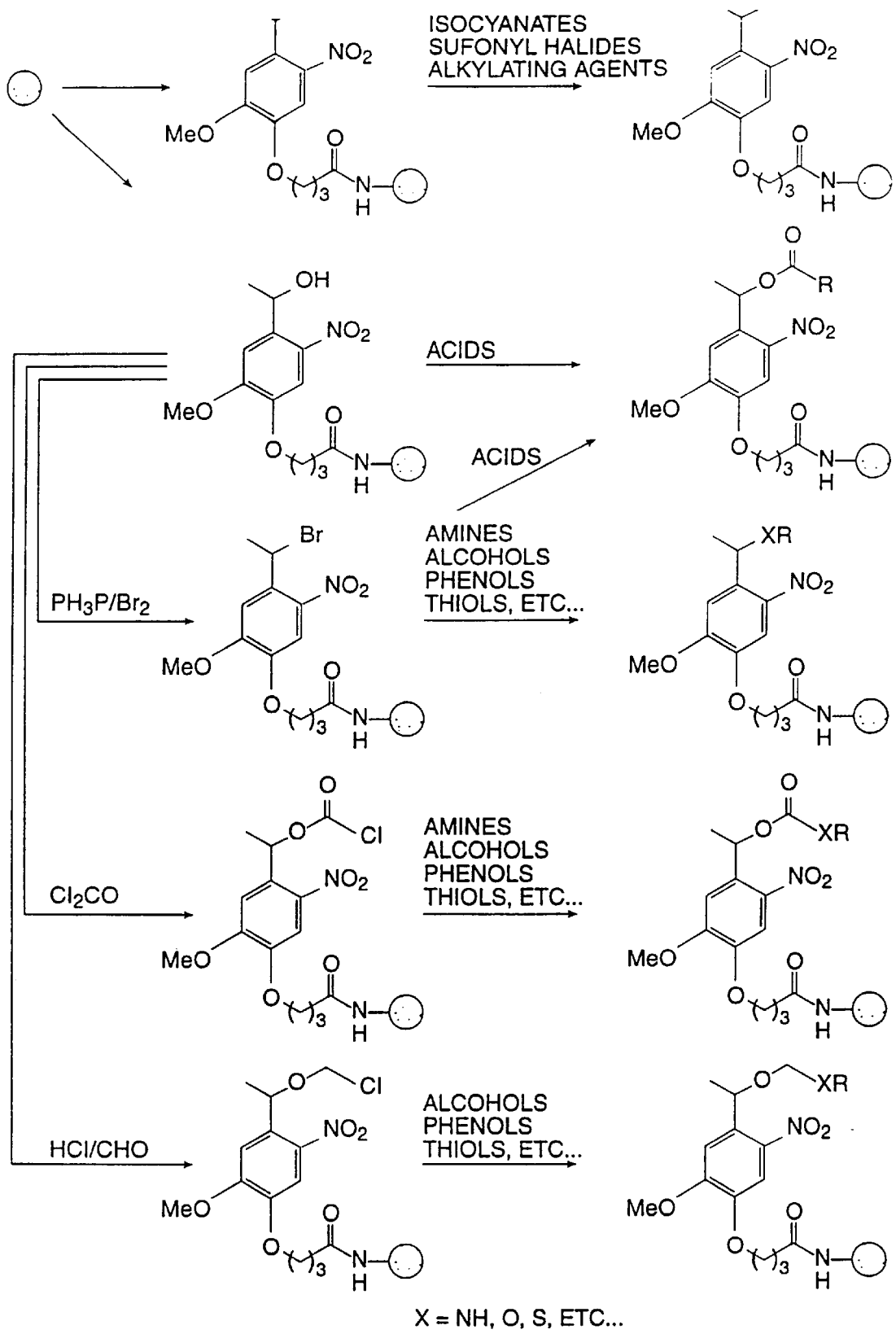
FIG. 4 illustrates several anchoring strategies for a variety of functionalities on the cleavable linker.

Various formats for attaching the molecules or building blocks to the linker are shown in FIG. 4. For example, when $X^{31}$ comprises a —NH$_2$ group, compounds bearing a carboxylic acid, isocyanate, carbonyls, or sulfonyl halide, and alkylating agents can be directly coupled to the amine functionality. Compounds bearing a carboxylic acid can be coupled directly to $X^{31}$ when it comprises a —OH group. Alternatively, the $X^{31}$ group can be converted to a halogen and preferably, a bromine, or various activating groups as shown in FIG. 4 for coupling to a variety of functionalities.

B. Small Molecule Ligand Synthesis

The photocleavable linkers described herein have been used in a variety of peptide and small molecule ligand solid phase syntheses. For example, pyrrolidines (see copending applications U.S. Ser. No. 08/264,137, filed Jun. 22, 1994, now abandoned, and U.S. Pat. No. 5,525,735); diketopiperazines (see copending applications U.S. Ser. No. 08/265,578, filed Jun. 23, 1994, now abandoned, and U.S. Ser. No. 08/393,318, filed Feb. 22, 1995, now abandoned); beta-lactams (see copending applications U.S. Ser. No. 08/344,275, filed Nov. 23, 1994, now abandoned, and U.S. Ser. No. 08/443,079, abandoned, filed May 17, 1995); and dihydropyridines, dihydropyrimidines, pyridines, and pyrimidines (see copending application U.S. Ser. No. 08/431,083, abandoned, filed Apr. 28, 1995), and libraries thereof, can be prepared using the photocleavable linkers described herein.

The photocleavable linkers described herein have been utilized in the synthesis and cleavage of a support-bound 4-thiazolidinone. See U.S. Pat. No. 5,549,974, PCT/US95/07988, each of which is incorporated herein by reference for all purposes. The stability of the linker and the 4-thiazolidinone towards typical TFA deprotection conditions was examined by incubating the thiazolidinone bound-support with a standard TFA-scavenger cocktail containing phenol, thioanisole, water, ethanedithiol, and TFA for 2 hours at room temperature. Analysis of the support by fast $^{13}$C NMR indicated that both components were stable to these conditions. Photolytic cleavage in pH 7.4 phosphate buffered saline (PBS) containing 5% DMSO (simulating a cleavage cocktail appropriate for transfer to a biological assay) was performed by irradiating for 3 hours with 365 nm UV light. The liberated 4-thiazolidinone was obtained in 95% purity and >90% yield.

Studies on model compounds in solution under identical conditions demonstrated that linker 9 cleaved 200–700 times faster than the ortho-nitrobenzyl support previously known and shown below:

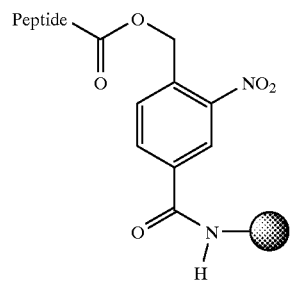

See Rich supra and Hammer supra.

C. Peptide Synthesis

The use of the photocleavable linkers described herein to assemble and cleave peptides has also been examined. For example, a cholecystokinin peptide (H-Met-Gly-Trp-Met-Asp-Phe-NH$_2$) bound to cleavable linker 9 was prepared in a stepwise fashion and then subjected to photolytic cleavage conditions. The peptide was assembled on the support with a TentaGel resin shown below:

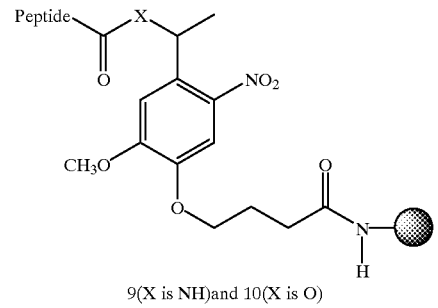

9(X is NH) and 10(X is O)

where X is O or X is NH, using Fmoc amino acids with standard chain protecting groups. After final Fmoc removal, the peptide was acylated with acetic anhydride before being side chain deprotected with TFA (containing phenol, water, thioanisole, and ethanedithiol). The supports were found to be quite stable to exposure of high concentrations of TFA (up to 100% for two hours.

Figure 3:
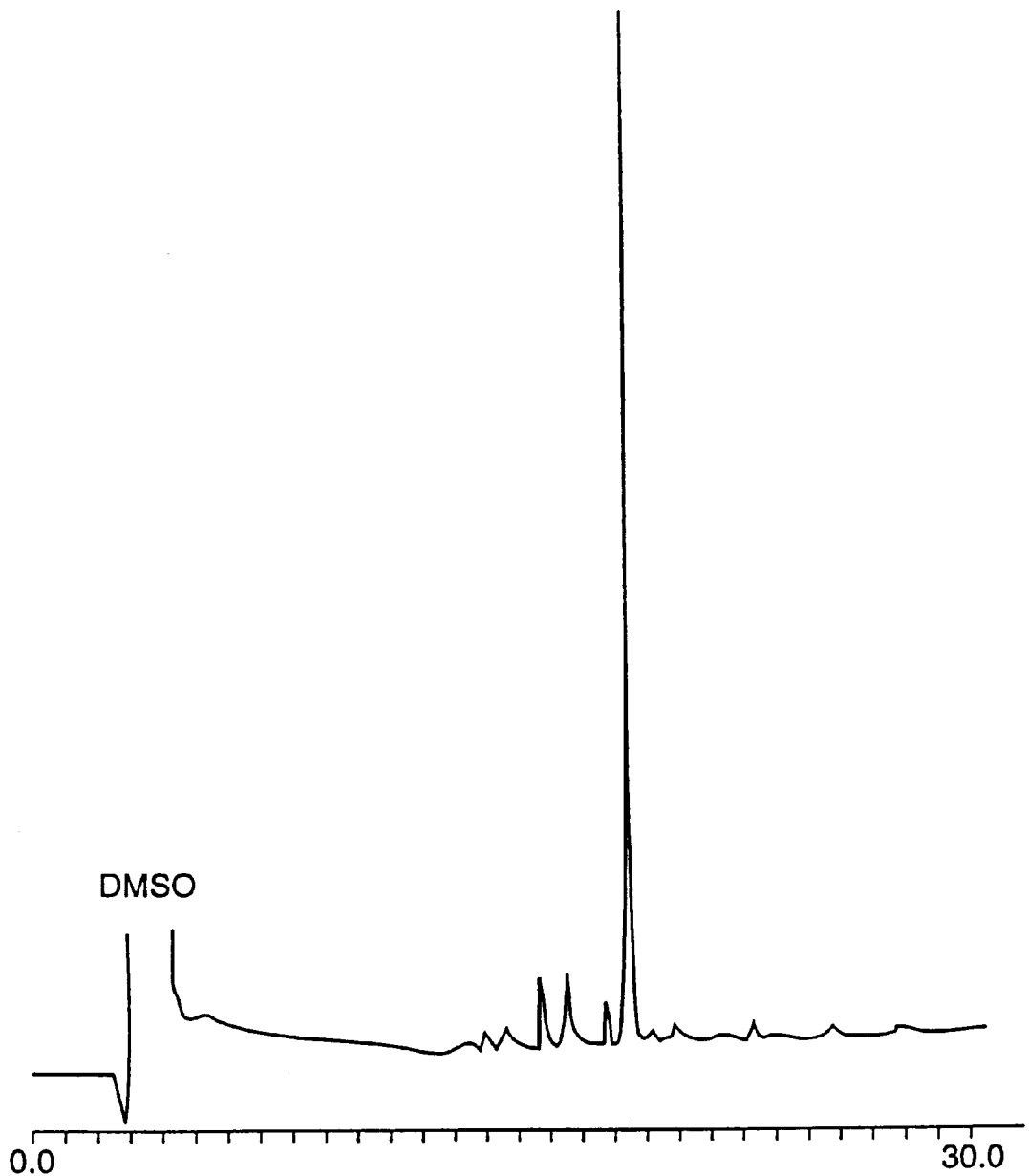
FIG. 3 illustrates the results achieved by the photolysis of a cholecystokinin peptide (H-Met-Gly-Trp-Met-Asp-Phe-NH₂) from a resin via photolysis. The peptide was synthesized on a resin having a photocleavable linking group.

The support-bound peptide was found to cleave with 1 hour of irradiation in the presence of hydrazine as scavenger to afford the desired CCK peptide in 86% purity (75% yield) with minimal amounts of oxidation. See FIG. 3. In the absence of hydrazine as scavenger, the peptide was of comparable purity, although the rate of cleavage was lower.

D. Use of Scavengers

The photocleavable linkers described herein produce nitroso-ketone byproducts upon photolysis. Although these byproducts remain attached to the support while the liberated compound diffuses away, they may still potentially trap the released compound or form chromogenic species which may act as internal light filters to slow the rate of cleavage. Accordingly, depending on the reaction scheme employed, in some embodiments, a scavenger is employed during the photolysis reaction, typically in the range of 10–100 mM. Preferred scavengers include hydrazine, ethanolamine, mercaptoethanol, and dithiothreitol. A particularly preferred scavenger is hydrazine.

III. General Methods

The compounds, compositions and methods of the present invention can be used in a number of solid phase synthesis applications, including light-directed methods, flow channel and spotting methods, pin-based methods and bead-based methods.

A. Bead Based Methods

A method which is particularly useful for synthesis of polymers and small ligand molecules on a solid support "bead based synthesis." A general approach for bead based synthesis is described copending application Ser. Nos. 07/762,522, (filed Sep. 18, 1991, now abandoned); U.S. Pat. No. 5,770,358; U.S. Pat. No. 5,639,603; U.S. Pat. No. 5,541,061 and PCT/US93/04145 (filed Apr. 28, 1993), Lam et al. (1991) Nature 354: 82–84; PCT application no. 92/00091 and Houghten et al., (1991) Nature 354: 84–86, each of which is incorporated herein by reference for all purposes.

A large plurality of beads are suspended in a suitable carrier (such as a solvent) in a parent container. The beads are provided with a photocleavable-linker having an active site. The active site is protected by an optional protecting group. In a first step of the synthesis, the beads are divided for coupling into separate containers. If present, the protecting groups are then removed and a first portion of the molecule to be synthesized is added to the various containers. For the purposes of this brief description, the number of containers will be limited to three, and the building blocks denoted as A, B, C, D, E, and F. The protecting groups are then removed and a first portion of the molecule to be synthesized, i.e., the first building block, is added to each of the three containers (i.e., A is added to container 1, B is added to container 2 and C is added to container 3).

Thereafter, the various beads are washed of excess reagents as appropriate, and remixed in the parent container. Again, it will be recognized that by virtue of the large number of beads utilized at the outset, there will similarly be a large number of beads randomly dispersed in the parent container, each having a particular first portion of the monomer to be synthesized on a surface thereof.

Thereafter, the various beads are again divided for coupling in another group of three containers. The beads in the first container are deprotected and exposed to a second building block (D), while the beads in the second and third containers are coupled to molecule portions E and F respectively. Accordingly, molecules AD, BD, and CD will be present in the first container, while AE, BE, and CE will be present in the second container, and molecules AF, BF, and CF will be present in the third container. Each bead, however, will have only a single type of molecule on its surface. Thus, all of the possible molecules formed from the first portions A, B, C, and the second portions D, E, and F have been formed.

The beads are then recombined into one container and additional steps such as are conducted to complete the synthesis of the molecules. A complete description of identifier tags for use in synthetic libraries is provided in U.S. Pat. No. 5,639,603 previously incorporated by reference for all purposes. Each bead, however, will have only a single type of molecule on its surface. In the particular embodiment described herein, all of the possible molecules formed from the various first, second, and third portions have been formed.

According to some embodiments, the solid support will bear an identifier tag. The identifier tag has a recognizable feature that is, for example, microscopically or otherwise distinguishable in shape, size, mass, charge, or color. This recognizable feature may arise from the optical, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library by reading the identifier tag. Particularly preferred identifier tags include synthetic oligodeoxyribonucleotides. For further detail on identifier tags, see U.S. Pat. No. 5,639,603 and U.S. Pat. No. 5,503,805. An example of a parallel synthesis of a thiazolidinone with an oligonucleotide tag is shown in FIG. 6 and described further below.

The identifier tags identify each reaction step that an individual library member or solid support has experienced and record the step in the synthesis series in which each chemical reaction was performed. The tags may be added immediately before, during, or after the chemical reaction, as convenient and compatible with the type of identifier tag, modes of attachment, and chemistry of molecular synthesis.

B. Light-Directed Methods

"Light-directed" methods (which are one technique in a family of methods known as VLSIPS™ methods) are described in U.S. Pat. No. 5,143,854, previously incorporated by reference. The light directed methods discussed in the '854 patent involve activating predefined regions of a substrate or solid support and then contacting the substrate with a preselected monomer solution. The predefined regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

In a similar manner to that described above, the solid support is then exposed to a receptor of interest that is appropriately labeled with, or coupled to another receptor with a label, such as a fluorescent or radioactive label. The solid support is then scanned to determine the location of the label. From knowledge of the composition of the molecule synthesized at each site, it becomes possible to identify the molecule(s) that are complementary to the receptor.

D. Other Methods

Photocleavable arrays also can be prepared using the pin approach developed by Geysen et al., for combinatorial solid-phase peptide synthesis. A description of this method is offered by Geysen et al., *J. Immunol. Meth.* (1987) 102: 259–274, incorporated herein by reference.

Additional methods applicable to library synthesis on a single substrate are described in U.S. Pat. Nos. 5,677,195 and 5,384,261, incorporated herein by reference for all purposes. In the methods disclosed in these applications, reagents are delivered to the substrate by either (1) flowing within a channel defined on predefined regions or (2) "spotting" on predefined regions. However, other apptoaches, as well as combinations of spotting and flowing, may be employed. In each instance, certain activated regions of the substrate are mechanically separated from other regions when the monomer solutions are delivered to the various reaction sites. Photocleavable linkers are particularly suitable for this technology as this delivery method may result in poor synthesis fidelity due to spreading, reagent dilution, inaccurate delivery, and the like. By using a photocleavable linker, rather than a conventional acid-cleavable linker, the purest material can be selectively cleaved from the surface for subsequent assaying or other procedures. More specifically, masks can be used when cleaving the linker to ensure that only linker in the center of the delivery area (i.e., the area where reagent delivery is most consistent and reproducible) is cleaved. Accordingly, the material thus selectively cleaved will be of higher purity than if the material were taken from the entire surface.

EXAMPLES

The following examples are included for the purpose of illustrating the invention and are not intended to limit the scope of the invention in any manner.

Example 1

This example illustrates the synthesis of the photochemically cleavable linking group 4-(4-(1-(9-Fluorenylmethoxycarbonylamino)ethyl)-2-methoxy-5-nitrophenoxy)butanoic acid.

A. Preparation of Methyl 4-((4-acetyl-2-methoxy)phenoxy) butanoate

A slurry of acetovanillone (41.00 g, 246.7 mmol), methyl 4-bromobutyrate (50.15 g, 277 mmol), and $K_2CO_3$ (51.3 g, 371 mmol) in 200 mL of DMF was stirred at room temperature for 16 hours. Water was added to the reaction mixture until all the $K_2CO_3$ was dissolved and the solution was then partitioned between EtOAc and saturated NaCl. The organic phase was dried ($MgSO_4$), filtered and evaporated to dryness to afford 68.40 g (100% crude yield) of the product ketoester as a light yellow oil, which slowly solidified, MP 48–49° C. Anal. Calcd. for $C_{14}H_{18}O_5$: C, 63.15; H, 6.81. Found: C, 62.81; H, 6.83.

B. Preparation of Methyl 4-(4-(1-hydroxyiminoethyl-2-methoxy)phenoxy)butanoate

To a solution of the keto ester from above (68.4 g) in 225 mL of 2:1 pyridine: $H_2O$ was added hydroxylamine hydrochloride (21.46 g, 309 mmol). After stirring at room temperature for 14 hours the reaction mixture was partitioned between EtOAc and saturated NaCl. The organic phase was dried ($MgSO_4$), filtered and evaporated to afford the oxime product as a white solid (69.94 g, 100% crude yield), MP 82–83° C. Anal. Calcd. for $C_{14}H_{19}NO_5$: C, 59.78; H, 6.81; N, 4.98. found: C, 59.62; H, 6.75; N, 4.81.

C. Preparation of Methyl 4-(4-(1-trifluoroacetamidoethyl-2-methoxy)phenoxy)-butanoate A slurry of the oxime from above (69.9 g, 146.7 mmol theoretical) and palladium catalyst (2.5 g of 10% on charcoal, Lancaster Synthesis Inc.) in 400 mL of glacial acetic acid was degassed twice with a water aspirator and placed under 1.1 atmosphere of hydrogen gas via a balloon. An additional 2 g of catalyst was added after 18 h and the balloon was refilled with hydrogen as the gas was consumed. An additional 2 g of catalyst was added after 2 days. The reaction mixture was filtered after 5 days and the solvent was removed under vacuum. The oily residue was taken up in 600 mL of water and acidified to pH 1 with 6N HCl. The aqueous phase was washed with $Et_2O$, then basified with solid NaOH to pH 11 and extracted with EtOAc. The EtOAc extract was dried ($MgSO_4$), filtered and evaporated to dryness to afford a crude amine as a colorless oil.

The crude amine was dissolved in 300 mL of pyridine, cooled to 0° C. with an ice bath, and was treated with trifluoroacetic anhydride (31 mL, 219 mmol) for 1 hour before being partitioned between EtOAc and saturated NaCl. The organic phase was dried ($MgSO_4$), filtered and evaporated to dryness to give the crude trifluoroacetamide as a light yellow solid. The solid was recrystallized from $CH_2Cl_2$/hexanes to afford 71.62 g of white solid (80% overall yield from acetovanillone), MP 96–97° C. Anal. Calcd. for $C_{16}H_{20}F_3NO_5$: C, 52.89; H, 5.55; N, 3.86. Found: C, 52.76; H, 5.45; N, 3.59.

D. Preparation of Methyl 4-(2-methoxy-5-nitro-4-(1-trifluoroacetamidoethyl)phenoxy)butanoate The trifluoroacetamide from above (9.40 g, 25.9 mmol) was dissolved in 200 mL of 70% $HNO_3$ cooled to 0° C. The solution turned orange in color and was quenched after 2 hours by pouring into water and adjusting the total volume to 2 L. The resultant slurry was chilled to 4° C. overnight and filtered to give a light yellow solid. Recrystalization from MeOH/$H_2O$ afforded 9.07 g (86% yield) of product as a light yellow solid, MP 156–157° C. Anal. Calc. for $C_{16}H_{19}F_3N_2O_7 \cdot 0.05$ $H_2O$: C, 46.96; H, 4.70; N, 6.85. Found: C, 46.59; H, 4.78; N, 6.89.

E. Preparation of 4-(4-(1-(9-Fluorenylmethoxycarbonylamino)ethyl)-2-methoxy-5-nitrophenoxy)butanoic acid To a solution of the nitro-phenyl compound from above (12.36 g, 30.27 mmol) in 250 mL of warm MeOH was added 1N NaOH (100 mL, 100 mmol) and the reaction mixture was heated to reflux for 5 hours. The solution was cooled to room temperature and concentrated to about 100 mL with a rotary evaporator. Dioxane (150 mL) and $H_2O$ (100 mL) were added and the pH of the solution was adjusted to pH 9 with 6N HCl. A solution of Fmoc-Cl (9.83 g, 38.0 mmol) in 100 mL of dioxane was added and an additional 15 mL of dioxane was added to create a homogeneous solution. The pH of the solution was measured to be 4.5 and was adjusted with 1N NaOH to pH 8 over the next 30 minutes. A light yellow precipitate formed as the pH was adjusted. The reaction was quenched after 18 h by adding 100 mL of 1N HCl and adjusting the total volume to 1 L with $H_2O$. The precipitate was collected, taken up in 1 L of hot EtOAc, dried over $MgSO_4$ and was filtered while hot. The solvent was removed under reduced pressure affording a light yellow solid which was triturated with 1 L of hot $Et_2O$. The solid was collected and was recrystallized from MeOH/10% hexanes to afford 12.78 g (81% yield for two steps) of product as a light yellow solid, MP 200–201° C. Anal. Calc. for $C_{28}H_{28}N_2O_8 \cdot H_2O$: C, 63.94; H, 5.48; N, 5.33. Found: C, 63.57; H, 5.44; N, 5.54.

Example 2

This example illustrates the photochemical cleavage of a series of linking groups.

Linking groups 1–6 were examined under photolysis conditions routinely employed for the synthesis of both peptides and oligonucleotides. Photolysis was carried out with a Hg(Xe) ARC lamp with a 350–450 nm dichroic reflector at an intensity of 10 mW/cm$^2$ at 365 nm. Roughly 90% of the UV light can be considered to be 365 nm in wavelength. The relative photolysis rates were measured in four different solvents (dioxane, methanol, pH 7.4 PBS, and pH 7.4 PBS containing 10 mM DTT). The substrate concentration was 0.1 mM and five time points were taken to determine the quantum yield and half-life for loss of starting material. The observed half-lives are shown in Table 1.

TABLE 1

Photolysis Half-Lives for Linkers 1–6

| Linking Group | Solvent | | | |
|---|---|---|---|---|
| | PBS | DTT/PBS | MeOH | Dioxane |
| 1 | 348 | 259 | a | a |
| 2 | 14.1 | 47.2 | 362 | 36.8 |
| 3 | 12.9 | 7.32 | 16.2 | 4.00 |
| 4 | 1.74 | 1.98 | 5.81 | 0.64 |
| 5 | 2.87 | 2.86 | 3.85 | 0.50 |
| 6 | 0.69 | 0.66 | 0.51 | 0.17 |

[a]No photolysis observed.

As the results in Table 4 indicate, linking groups 3–6 show acceptable rates of photolysis in typical aqueous buffers. Additionally, linking groups 3 and 4 were examined for stability to TFA treatment which is used in some methods of solid phase polymer synthesis (i.e., a "Merrifield"-type peptide synthesis, Fmoc-based peptide synthesis and spotting and flow channel methods associated with VLSIPS™). Linking groups 3 and 4 were each dissolved in both 50% TFA/$CH_2Cl_2$ and 95% TFA/$H_2O$ for one hour. No decomposition of either linking group was observed by HPLC.

Example 3

This example illustrates the synthesis of thiazolidinones on a resin having a photocleavable linker and the subsequent removal of the thiazolidinones from the resin via photolysis.

A. Thiazolidinone Preparation

Commercially available $H_2$N-S-TentaGel (Rapp Polymere, Tübingen, Germany, 1 g, 0.30 mmol/g loading) was washed with DMF and treated with 3 mL of a 0.15 M solution of OBt-activated Fmoc-photolinker (prepared from 310 mg of Fmoc-linker, 92 mg of HOBt, 95 µL of DIC in 3 mL of DMF) for 1.5 hour. Ninhydrin test indicated a complete reaction had taken place. The resin was washed with DMF and $CH_2Cl_2$, and was then capped by treatment with 20% $Ac_2O$ and 30% pyridine in 50% $CH_2Cl_2$ for 30 minutes. The resin was washed (3×5 mL DMF, 3×5 mL $CH_2Cl_2$), and dried under vacuum for 1 hour. A portion of the resin (200 mg) was deprotected with 30% piperidine/DMF for 30 minutes and then washed with DMF. A 0.5M solution of Fmoc-Glycine symmetrical anhydride (prepared from 182 mg of Fmoc-Gly-OH and 50 µL of DIC in 0.6 mL of DMF) was coupled to the resin for 1 hour, by which time ninhydrin had revealed that a complete reaction had taken place. The resin was washed and capped as above for 30 minutes. Deprotection with piperidine, washing and drying as above gave roughly 150 mg of dry resin. The dried resin was partitioned (roughly 40 mg of resin per vial) into 24 -mL vials equipped with a screw top closure. ACN (2 mL) and 3 A molecular sieves (20–30 pellets) were added to each vial. Benzaldehyde (152 µL) and mercaptoacetic acid (300 µL) was added to the first vial whereas 2,4-dimethoxybenzaldehyde (250 mg) and mercaptoacetic acid (300 µL) was added to the second vial. Both vials were heated to 70° C. for 2 hours. The vials were cooled to room temperature and the resin was transferred to disposable filter tubes and washed extensively (3×5 mL $CH_2Cl_2$, 3×5 mL DMF, 3×5 mL $CH_2Cl_2$, 3×5 mL MeOH, 3×5 mL $CH_2Cl_2$, 3×5 mL $Et_2O$).

B. General Photolysis Conditions

Roughly 2–20 mg of resin were placed in plastic centrifuge tubes equipped with 0.22 µm membrane filters (Ultrafree-MC Filter Units from Millipore, Bedford, Mass.) and were suspended in 100 µL of pH 7.4 PBS buffer. Photolysis were conducted with a 500 W Hg ARC lamp fitted with a 350–450 nm dichroic mirror at a 10 mW/$cm^2$ power level measured at 365 nm. The samples were irradiated from above for various times with gentle mixing from an orbital shaker table. After photolysis the samples centrifuged and the filtrate collected. The samples were washed with 100 µL of 50% ACN/$H_2O$ and again centrifuged. The collected filtrates from each sample were analyzed by HPLC for the presence of thiazolidinone. See FIG. 2A–2D. The data indicated that both the thiazolidinones were produced in high purity on the resin and that they were stable to the photolysis conditions.

C. Stability towards TFA treatment $H_2$N-S-TentaGel (500 mg) was elaborated in analogy to Example 3 with Fmoc-Gly-OH labeled at the α-carbon with $^{13}$C (2 $^{13}$C, 99% from Cambridge Isotope Laboratories, Inc., Andover, Mass.) The resin was capped with $Ac_2O$ as above, deprotected with piperidine, and the Fmoc-photolinker coupled as its OBt-activated ester. The resin was again capped, deprotected, and reacted with unlabeled Fmoc-Glycine-OH as its anhydride. An additional round of capping and deprotection generated the free amine resin. Reaction with 0.75M PhCHO labeled at the carbonyl (carbonyl-$^{13}$C, 99% from Cambridge Isotope Laboratories, Inc., Andover, Mass.) and 2.0M mercaptoacetic acid in ACN containing 3 Å molecular sieves for 2 hours at 70° C. generated the double labeled thiazolidinone resin. The resin was washed extensively (3×5 mL $CH_2Cl_2$, 3×5 mL DMF, 3×5 mL $CH_2Cl_2$, 3×5 mL MeOH, 3×5 mL $CH_2Cl_2$, 3 ×5 mL $Et_2O$) and dried under vacuum.

A portion (20 mg) of the resin was treated with 95% TFA/5% $H_2O$ for 1 hour, followed by washing with $CH_2Cl_2$, MeOH, and $Et_2O$. Gel $^{13}$C NMR analysis of the resin indicated no loss of thiazolidinone, as evidenced by relative integration of the two labeled carbons. Any destruction of either the photolinker or thiazolidinone would be expected to result in the integration of the benzylic carbon to decrease. This experiment demonstrated that both the photolinker and thiazolidinone were stable to TFA treatment.

D. Additional Stability Experiments

In a separate experiment, an additional 20 mg of resin was treated for 2 hours at room temperature with a solution of phenol (75 mg), thioanisole (50 µL), water (50 µL), ethanedithiol (25 µL), and TFA (1 mL) followed by washing as above. Gel $^{13}$C NMR analysis of the resin indicated no loss of thiazolidinone or photolabile linker, as evidenced by the relative integration of the two labeled carbons.

Example 4

This example illustrates the synthesis of a CCK peptide on a resin having a photocleavable linker and the subsequent removal of the peptide from the resin via photolysis.

A. Preparation of the CCK Peptide

The peptide H-Met-Gly-Trp-Met-Asp-Phe was prepared on TentaGel resin (25 mg) bearing the photolabile linker 9 according to the synthesis cycle described below. All amino acids were N-Fmoc protected. The side chain functionalities of Asp and Trp were protected as the tert-butyl ester and Boc carbamate, respectively.

B. Coupling

To a 0.11M solution of amino acid in DMF (0.50 mL) were added 0.20M HATU in DMF (0.25 mL) and 0.60M N,N-diisopropylethylamine in DMF (0.25 mL). The resulting solution was added to TentaGel bearing an unprotected amine, and the suspension was stirred at room temperature. After 20 minutes, the supernatant was decanted and the resin washed successively with DMF and THF.

C. Capping

To the resin was added a commercially prepared solution of N-methylimidazole (16%) in THF (0.5 mL) followed by a commercially prepared solution of acetic anhydride (10%) and 2,6-lutidine (10%) in THF (0.50 mL). The resulting suspension was stirred 5 minutes at room temperature. The supernatant was then decanted and the resin washed successively with THF and DMF.

D. Amine Deprotection

Piperidine (20% in DMF, 1.00 mL) was added to the resin and the resulting suspension was stirred 10 minutes at room temperature. The supernatant was then decanted and the resin washed with DMF.

Following Fmoc removal from the final methionine residue, the resin was washed thoroughly with THF and the solvent evaporated. Side chain protection was removed by treating the resin with 1000:75:50:50:25 TFA/phenol/water/thioanisole/ethanedithiol (0.40 mL) and allowing the resulting suspension to stand 1 hour at room temperature with occasional agitation.

E. Photolytic Release

50 Beads bearing the fully-deprotected peptide were placed in one well of a 96-well polystyrene microfiter plate and covered with 75 μL of a 1:1 solution of DMSO and PBS containing 0.1% hydrazine. A glass slide was fixed on top of the plate, which was then irradiated for one hour. After irradiation, the supernatant was decanted from the beads and analyzed directly by reverse phase HPLC, as show in FIG. 3. The product peptide, which co-eluted with authentic material, was obtained in 70% yield. MS (ESI) m/z 786 $(MH^{+})$.

Example 5

This example illustrates the preparation of a bromo-photocleavable linker on a resin.

TentaGel S $NH_2$ (10 g, 130 μm particle size, 0.29 mmol/g loading; from Rapp Polymere, Tubingen Germany) was washed with DMF (50 mL) and treated with 30% piperidine in DMF (20 mL) for 10 minutes. The resin was then extensively washed with DMF and treated with a 0.5M solution of DIC/HOBt-activated alcohol photolinker (prepared as above from 2.26 g (7.55 mmol) of 4-(4-(1-hydroxyethyl)-6-methoxy-3-nitrophenoxy)butyric acid, HOBt (1.2 g, 8.88 mmol), a solution of DIC in DMF (1.20 mL, 7.66 mmol) in DMF (15 mL) for 18 hours. Conventional ninhydrin colorimetric test indicated that complete acylation of the resin had taken place. The resin was washed with DNU (100 mL), $CH_2Cl_2$ (100 mL), methanol (100 mL), and diethyl ether (50 mL), and was dried overnight in vacuo.

A 2.5 g aliquot of the above resin was suspended in $CH_2Cl_2$ for 30 minutes, filtered, and was then treated with 12 mL of a 0.25M solution of triphenylphosphine dibromide (Lancaster Synthesis, Windham, N.H.) in $CH_2Cl_2$ for 4 hours. The resin was washed with $CH_2Cl_2$ (10 mL), DMF (10 mL), $CH_2Cl_2$ (10 mL), methanol (10 mL), DMF (10 mL) and was then capped by treatment with 0.25M acetic anhydride/0.75M pyridine in DMF for 30 minutes. The resin was washed as above and dried overnight in vacuo to give the bromolinker resin.

Example 6

This example illustrates the synthesis of a representative derivatizing group, FMOC-15-ATOM-PEG To a solution of 2,2'-(ethylenedioxy)-diethylamine (75 mL, 511 mmol) (Fluka Chemie AG, Switzerland) in 1 L of dry p-dioxane was slowly added a solution of glutaric anhydride (11.4 g, 100 mmol) in 100 mL of dry p-dioxane over 1 hour. A viscous white oil formed during the reaction. The solvent was decanted and the oil was triturated with acetone, followed by trituration twice with ethyl ether (until ether phase remains clear). This oily residue was then carried on to the next step without further purification.

A slurry containing the amino acid from above, diisopropylethylamine (52 mL, 299 mmol) and trimethylsilyl chloride (25 mL, 197 mmol) in 300 mL of $CH_2Cl_2$ was heated to reflux for 3 h, during which time the solution became homogeneous. The reaction mixture was cooled to 0° C. and FMOC-Cl (27 g, 104 mmol) was added over a four hour period in three equal aliquots. The reaction mixture was allowed to warm to room temperature and stirred for an additional 3 h. The solvent was removed under reduced pressure and the residue was partitioned between $Et_2O$ and 5% $NaHCO_3$. The organic phase was discarded and the aqueous phase was acidified to pH 2 with 1N HCl, and extracted with EtOAc. The organic extract was washed (1N HCl and saturated NaCl), dried ($MgSO_4$), and evaporated to dryness under reduced pressure. Chromatography on silica gel (5% to 20% AcOH in EtOAc) afforded 32.7 g (65% yield for two steps) of the desired product, N-FMOC-N-glutaryl-2,2'-(ethylenedioxy)diethylamine, as a colorless oil which slowly solidified.

Example 7

This example illustrates the synthesis of beta-lactams on a resin having a photocleavable linker and the subsequent removal of the beta-lactams from the resin via photolysis.

Sasrin-immobilized Fmoc-protected photolinker was prepared as described above. The resin was deprotected with 30% piperidine/DMF for 75 minutes and then washed with DMF.

To a suspension of the deprotected photolinker (35 mg) in trimethyl orthoformate (1 ml) wa added t-butyl glyoxalate (50 mg). The reaction was heated at 70° C. for 3 hours with frequent shaking. The reaction mixture was cooled, filtered, washed, and dried to yield the corresponding imine.

The 3-phthalimido-2-azetidinone was prepared by treating the imine with phthalimido acetyl chloride (25 equivalents) and triethylamine (30 equivalents) at 0° C. The resin was transferred into a centrifuge filter unit, washed (4×2 mL methylene chloride, 2×2 mL methanol, 3×2 mL diethyl ether) and dried under high vacuum for 30 minutes.

Figure 5:
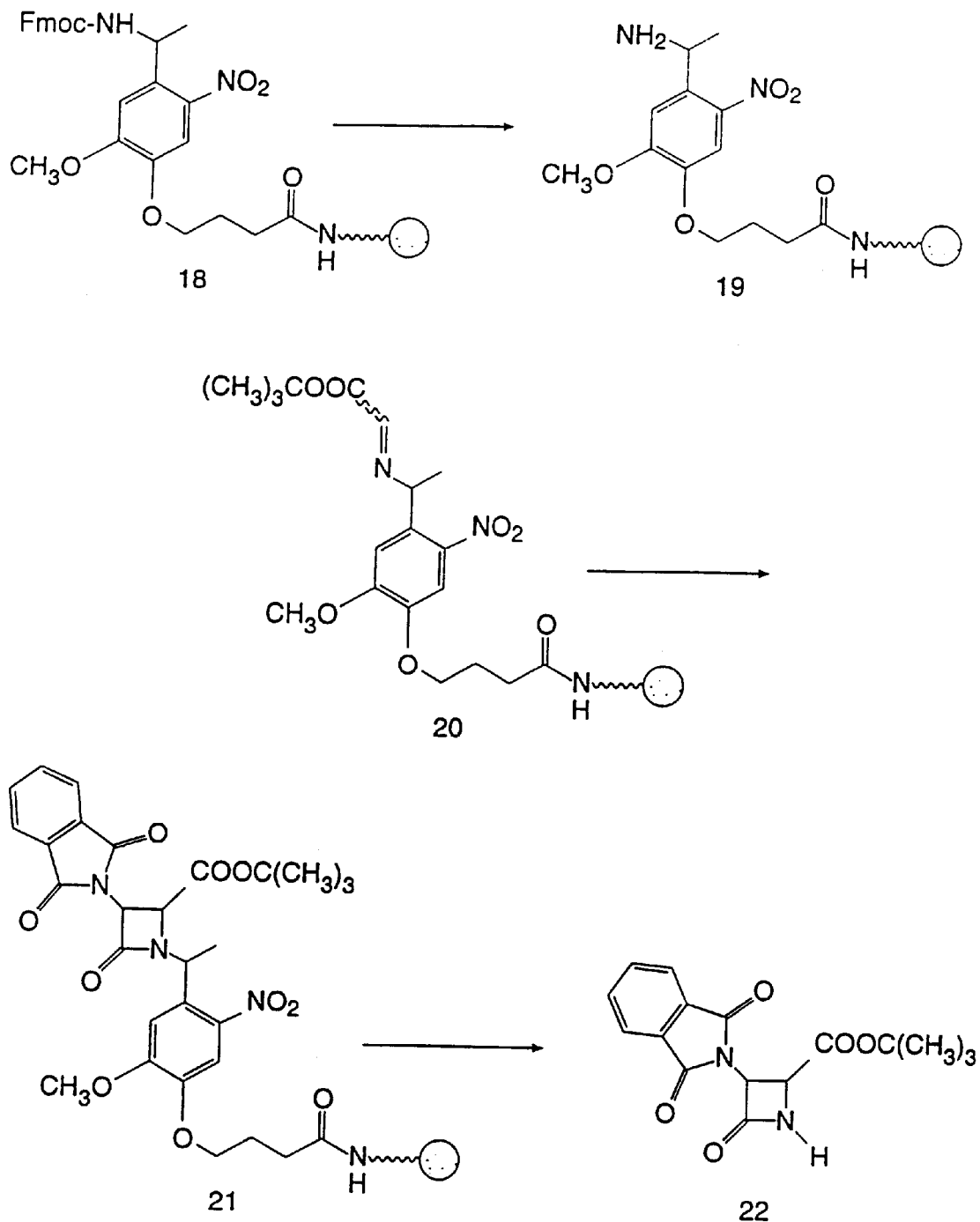
FIG. 5 provides a schematic illustration of the solid phase synthesis of a beta-lactam using photocleavable linker 9.

The β-lactam was cleaved from the resin through photolysis in ethanol or DMSO using a 500 W Hg ARC lamp fitted with a 350–450 nm dichroic mirror at a 10 $mW/cm^2$ power level measured at 365 nm. After photolysis, the samples were filtered and the filtrate was collected. The samples were analyzed by HPLC, mass spectroscopy and NMR and the data indicated that the desired β-lactam was produced in high purity. This reaction sequence is shown schematically in FIG. 5.

The above description is illustrative and not restrictive. Many variations of the invention will become apparent to those of skill in the art upon review of this disclosure. Merely by way of example a wide variety of process times, reaction temperatures, and other reaction conditions may be utilized, as well as a different ordering of certain processing steps. The scope of the invention should, therefore, be determined not with reference to the above description, but instead should be determined with reference to the appended claims along with their full scope of equivalents. Although certain embodiments and examples have been used to describe the invention, changes may be made to those embodiments and examples without departing from the scope of the following claims or spirit of the invention.

The disclosures in this application of all articles and references, including patent documents, are incorporated herein by reference.

What is claimed is:

1. A composition having the formula:

A—B—L wherein A is a solid substrate, B is a bond or a derivatizing group, and L is a photocleavable linking group having the formula:

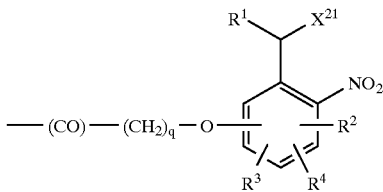

wherein,

R$^1$ is hydrogen, C$_1$–C$_8$ alkyl, aryl or arylalkyl; R$^2$, R$^3$ and R$^4$ are each independently hydrogen, C$_1$–C$_8$ alkyl, or C$_1$–C$_8$ alkoxy; X$^{21}$ is halogen, —SH, —SP, —OH, —NH$_2$, —OP or —NHP, wherein P is a suitable protecting or activating group; and q is an integer of from 1 to 10.

2. The composition of claim 1, wherein the derivatizing group comprises an amino acid, peptide, or polyether chain having an amine functionality at the termini.

3. The composition of claim 2, wherein the derivatizing group is selected from the group consisting of a bond, —NH—(CH$_2$CH$_2$O)$_n$CH$_2$CH$_2$NH—, —NH—CH$_2$(CH$_2$CH$_2$O)$_n$CH$_2$CH$_2$CH$_2$NH—, —NH—CH$_2$(CH$_2$CH$_2$CH$_2$O)$_n$CH$_2$CH$_2$CH$_2$NH— or —NH—(CH$_2$)$_m$O(CH$_2$)$_n$O(CH$_2$)$_m$NH—, in which n is an integer of from 1 to 10 and m is an integer of from 1 to 6.

4. The composition of claim 3, wherein the derivatizing group is —NH—(CH$_2$CH$_2$O)$_2$CH$_2$CH$_2$NH—.

5. The composition of claim 1, wherein L has the formula:

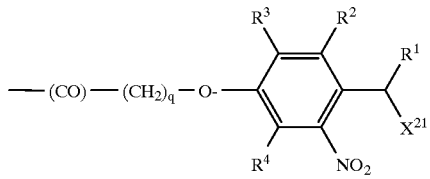

wherein,

R$^1$ is hydrogen, or C$_1$–C$_8$ alkyl; R$^2$ and R$^4$ are each independently hydrogen, C$_1$–C$_8$ alkyl or C$_1$–C$_8$ alkoxy; R$^3$ is C$_1$–C$_8$ alkoxy; X$^{21}$ is —Br, —Cl, —OH, —OP, —SH, —SP, —NH$_2$ or —NHP, wherein P is a suitable protecting or activating group; and q is an integer of from 1 to 4.

6. The composition of claim 1, wherein L has the formula:

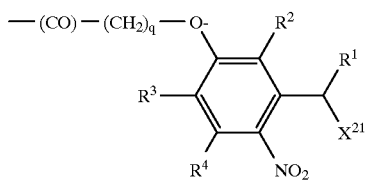

wherein,

R$^1$ is hydrogen, or C$_1$–C$_8$ alkyl; R$^2$ and R$^4$ are each independently hydrogen C$_1$–C$_8$ alkyl or C$_1$–C$_8$ alkoxy; R$^3$ is C$_1$–C$_8$ alkoxy; X$^{21}$ is —Br, —Cl, —OH, —OP, —SH, —SP, —NH$_2$ or —NHP, wherein P is a suitable protecting or activating group; and an integer of from 1 to 4.

7. The composition of claim 5 or 6, wherein R$^1$ is methyl and R$^3$ is methoxy.

8. The composition of claim 7, wherein R$^1$ is methyl, R$^3$ is methoxy, and R$^2$ and R$^4$ are each hydrogen.

9. The composition of claim 8, wherein n is 3, R$^1$ is methyl, R$^3$ is methoxy, R$^2$ and R$^4$ are each hydrogen, and X$^{21}$ is —OH, —ODMT, —O(CO)Cl, —OCH$_2$Cl, —O(CO)OAr, —OAc, —NH$_2$, —NH-Fmoc, —NHAc, or —NH-BOC.

10. The composition of claim 9, wherein R$^1$, R$^2$ and R$^4$ are hydrogen, R$^3$ is methoxy, and X$^{21}$ is —Br, and q is 1;

wherein R$^1$, R$^2$ and R$^4$ are hydrogen, R$^3$ is methoxy, and X$^{21}$ is —Br, and q is 3;

wherein R$^1$, R$^2$ and R$^4$ are hydrogen, R$^3$ is methoxy, and X$^{21}$ is —OH, and q is 1;

wherein R$^1$, R$^2$ and R$^4$ are hydrogen, R$^3$ is methoxy, and X$^{21}$ is —OH, and q is 3;

wherein R$^1$, R$^2$ and R$^4$ are hydrogen, R$^3$ is methoxy, and X$^{21}$ is —OAc, and q is 1;

wherein R$^1$, R$^2$ and R$^4$ are hydrogen, R$^3$ is methoxy, and X$^{21}$ is —OAc, and q is 3;

wherein R$^1$, R$^2$ and R$^4$ are hydrogen, R$^3$ is methoxy, and X$^{21}$ is —NH$_2$, and q is 1;

wherein R$^1$, R$^2$ and R$^4$ are hydrogen, R$^3$ is methoxy, and X$^{21}$ is —NH$_2$, and q is 3;

wherein R$^1$, R$^2$ and R$^4$ are hydrogen, R$^3$ is methoxy, and X$^{21}$ is —NAc, and q is 1;

wherein R$^1$, R$^2$ and R$^4$ are hydrogen, R$^3$ is methoxy, and X$^{21}$ is —NAc, and q is 3;

wherein R$^1$, R$^2$ and R$^4$ are hydrogen, R$^3$ is methoxy, and X$^{21}$ is —NHFmoc, and q is 1;

wherein R$^1$, R$^2$ and R$^4$ are hydrogen, R$^3$ is methoxy, and X$^{21}$ is —NHFmoc, and q is 3;

wherein R$^1$, R$^2$ and R$^4$ are hydrogen, R$^3$ is methoxy, and X$^{21}$ is —O(CO)Cl, and q is 1;

wherein R$^1$, R$^2$ and R$^4$ are hydrogen, R$^3$ is methoxy, and X$^{21}$ is —O(CO)Cl, and q is 3;

wherein R$^1$, R$^2$ and R$^4$ are hydrogen, R$^3$ is methoxy, and X$^{21}$ is —OCH$_2$Cl, and q is 1;

wherein R$^1$, R$^2$ and R$^4$ are hydrogen, R$^3$ is methoxy, and X$^{21}$ is —OCH$_2$Cl, and q is 3;

wherein R$^1$ is methyl, R$^2$ and R$^4$ are hydrogen, R$^3$ is methoxy, and X$^{21}$ is —Br, and q is 1;

wherein R$^1$ is methyl, R$^2$ and R$^4$ are hydrogen, R$^3$ is methoxy, and X$^{21}$ is —Br, and q is 3;

wherein $R^1$ is methyl, $R^2$ and $R^4$ are hydrogen, $R^3$ is methoxy, and $X^{21}$ is —OH, and q is 1;

wherein $R^1$ is methyl, $R^2$ and $R^4$ are hydrogen, $R^3$ is methoxy, and $X^{21}$ is —OH, and q is 3;

wherein $R^1$ is methyl, $R^2$ and $R^4$ are hydrogen, $R^3$ is methoxy, and $X^{21}$ is —OAc, and q is 1;

wherein $R^1$ is methyl, $R^2$ and $R^4$ are hydrogen, $R^3$ is methoxy, and $X^{21}$ is —OAc, and q is 3;

wherein $R^1$ is methyl, $R^2$ and $R^4$ are hydrogen, $R^3$ is methoxy, and $X^{21}$ is —NH$_2$, and q is 1;

wherein $R^1$ is methyl, $R^2$ and $R^4$ are hydrogen, $R^3$ is methoxy, and $X^{21}$ is —NH$_2$, and q is 3;

wherein $R^1$ is methyl, $R^2$ and $R^4$ are hydrogen, $R^3$ is methoxy, and $X^{21}$ is —NAc, and q is 1;

wherein $R^1$ is methyl, $R^2$ and $R^4$ are hydrogen, $R^3$ is methoxy, and $X^{21}$ is —NAc, and q is 3;

wherein $R^1$ is methyl, $R^2$ and $R^4$ are hydrogen, $R^3$ is methoxy, and $X^{21}$ is —NHFmoc, and q is 1;

wherein $R^1$ is methyl, $R^2$ and $R^4$ are hydrogen, $R^3$ is methoxy, and $X^{21}$ is —NHFmoc, and q is 3;

wherein $R^1$ is methyl, $R^2$ and $R^4$ are hydrogen, $R^3$ is methoxy, and $X^{21}$ is —O(CO)Cl, and q is 1;

wherein $R^1$ is methyl, $R^2$ and $R^4$ are hydrogen, $R^3$ is methoxy, and $X^{21}$ is —O(CO)Cl, and q is 3;

wherein $R^1$ is methyl, $R^2$ and $R^4$ are hydrogen, $R^3$ is methoxy, and $X^{21}$ is —OCH$_2$Cl, and q is 1; or wherein $R^1$ is methyl, $R^2$ and $R^4$ are hydrogen, $R^3$ is methoxy, and $X^{21}$ is —OCH$_2$Cl, and q is 3.

11. The composition of claim 10, wherein $R^1$ is methyl, $R^2$ and $R^4$ are hydrogen, $R^3$ is methoxy, and $X^{21}$ is —OH, and q is 3; or wherein $R^1$ is methyl, $R^2$ and $R^4$ are hydrogen, $R^3$ is methoxy, and $X^{21}$ is —NH$_2$, and q is 3.

12. A method of synthesizing small ligand molecules or peptides on a solid support having optional spacers, said small ligand molecules or peptides being removable therefrom upon application of a suitable energy source, said method comprising the steps of:

(a) providing on the surface of said solid support, a photolabile linking group of formula:

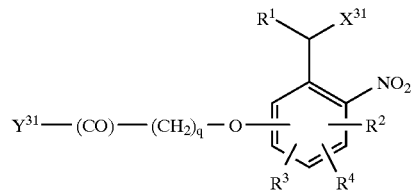

wherein, $R^1$ is hydrogen, $C_1$–$C_8$ alkyl, aryl or arylalkyl; $R^2$, $R^3$ and $R^4$ are each independently hydrogen, $C_1$–$C_8$ alkyl or $C_1$–$C_8$ alkoxy; $X^{31}$ is halogen, —OH, —OP, —SH, —SP, —NH$_2$ or —NMP and $Y^{31}$ is Br, Cl, OH, NH$_2$, SH, OP, SP and NHP, wherein P is a protecting or activating group; and q is an integer of from 1 to 10, to produce a derivatized solid support having attached photolabile linking groups suitably protected with protecting groups;

(b) optionally removing said protecting groups from said derivatized solid support to provide a derivatized solid support having photolabile linking groups with synthesis initiation sites;

(c) optionally activating said solid support to provide a derivatized solid support having photolabile linking groups with activated synthesis sites; and (d) coupling a first building block to said synthesis initiation sites on said derivatized solid support to produce a solid support having attached building block which is removable therefrom upon application of said energy source.

* * * * *